United States Patent [19]
Carlson et al.

[11] Patent Number: 6,117,855
[45] Date of Patent: Sep. 12, 2000

[54] USE OF A NK-1 RECEPTOR ANTAGONIST AND AN ANTIDEPRESSANT AND/OR AN ANTI-ANXIETY AGENT

[75] Inventors: Emma Joanne Carlson, Puckeridge; Nadia Melanie Rupniak, Bishops Stortford, both of United Kingdom

[73] Assignee: Merck Sharp & Dohme Ltd., Hoddesdon, United Kingdom

[21] Appl. No.: 08/994,063

[22] Filed: Dec. 19, 1997

Related U.S. Application Data

[63] Continuation-in-part of application No. PCT/GB97/02748, Oct. 7, 1997.

[30] Foreign Application Priority Data

| Oct. 7, 1996 | [GB] | United Kingdom | 9620880 |
| Aug. 4, 1997 | [GB] | United Kingdom | 9716458 |
| Aug. 4, 1997 | [GB] | United Kingdom | 9716460 |

[51] Int. Cl.⁷ ............... A61K 31/675; A61K 31/535; A61K 31/44; A61K 31/445
[52] U.S. Cl. .......... 514/90; 514/236.2; 514/278; 514/329
[58] Field of Search ............... 514/90, 236.2, 514/278, 329

[56] References Cited

U.S. PATENT DOCUMENTS

| 5,162,339 | 11/1992 | Lowe, III . | |
| 5,538,982 | 7/1996 | Hagan et al. . | |
| 5,612,337 | 3/1997 | Baker et al. . | |
| 5,716,942 | 2/1998 | Dorn et al. | 514/90 |
| 5,719,147 | 2/1998 | Dorn et al. . | |
| 5,728,695 | 3/1998 | Harrison et al. . | |

FOREIGN PATENT DOCUMENTS

| 0 577 394 | 1/1994 | European Pat. Off. . |
| WO 95/08549 | 3/1995 | WIPO . |
| WO 95/18124 | 7/1995 | WIPO . |
| WO 96/05181 | 2/1996 | WIPO . |
| WO 96/18643 | 6/1996 | WIPO . |
| WO 96/19233 | 6/1996 | WIPO . |
| WO 96/24353 | 8/1996 | WIPO . |

OTHER PUBLICATIONS

Aguiar, M., et al., *Physiology & Behavior*, 1996, 60 (4) 1183–1186.
Barden, N., et al., *J. Neurochem.*, 1983, 41, 834–840.
Bristow, L., et al., *Eur. J. Pharmacol.*, 1994, 253, 245–252.
Brodin, E., et al., *Neuropharmacology*, 1987, 26 (6) 581–590.
Brodin, E., et al., *Neuropeptides*, 1994, 26, 253–260.
Culman, J., et al., *J. Physiol. Pharmacol.*, 1995, 73, 885–891.
Cutler, et al., *J. Psychopharmacol*, 1994, 8, A22, 87.
Elliott, P. J., *Exp. Brain Res. UK*, 1988, 73, 354–356.
*F–D–C Reports—Prescription Pharmaceuticals and Biotechnology*, Dec. 8, 1997, 59 (49), 10.
File, S. E., *Pharm. Biochem. Behavior*, 1997, 58, 3, 747–752.
Kramer, et al., *Science*, 1998, 281, 1640–1645.
Lowe, J., et al., *Drug News Perspect*, 1992, 5 (4), 223.
Malek–Ahmadi, *Neuroscience and Behavioral Reviews*, 1992, 16, 365–359.
Rimon, R., et al., *Biological Psychiatry*, 1984, 19(4), 509–516.
Roccon, et al., *Pharmacological Research*, 1995, 31, 191.
Rupniak, N., et al., *Eur. J. Pharmacol.*, 1994, 265, 179–183.
Shaikh, M., et al., *Brain Research*, 1993, 625, 283–294.
Shirayama, Y., et al., *Brain Research*, 1996, 739, 70–78.
Siegel, R., et al., *Neurochem. Int.*, 1984, 6 (6), 783–789.
Siegel, A., et al., *Aggressive Behavior*, 1995, 21, 49–62.
Teixeira, R., et al., *European J. Pharm.*, 1996, 311, 7–14.
Vassout, et al., *Neuropeptides*, 1994, 26 (Suppl. 1), 38.
Wahlestedt, *Science*, 1998, 281, 1624–1625.
*Wall Street Journal*, Aug. 13, 1998, B1, Col. 2.

*Primary Examiner*—William R. A. Jarvis
*Attorney, Agent, or Firm*—J. Eric Thies; David L. Rose

[57] ABSTRACT

The present invention relates to the treatment or prevention of depression and/or anxiety by the administration of a combination of CNS-penetrant NK-1 receptor antagonists and an antidepressant or anti-anxiety agent.

14 Claims, 2 Drawing Sheets is no clear direction from WO 96/24353 to which class of
USE OF A NK-1 RECEPTOR ANTAGONIST AND AN ANTIDEPRESSANT AND/OR AN ANTI-ANXIETY AGENT

CROSS REFERENCE TO RELATED APPLICATIONS

This application is a continuation-in-part of copending PCT Application No. PCT/GB97/02748, filed Oct. 7, 1997, which claims priority from Great Britain Application No. 9620880.6, filed Oct. 7, 1996, Great Britain Application No. 9716458.6, filed Aug. 4, 1997, and Great Britain Application No. 9716460.2, filed Aug. 4, 1997.

This invention relates to the treatment or prevention of depression and/or anxiety by the administration of a combination of a specific class of NK-1 receptor antagonists and an antidepressant or anti-anxiety agent. The present invention also provides preclinical screens for anxiolytic and antidepressant activity of NK-1 receptor antagonists.

Major depression is characterised by feelings of intense sadness and despair, mental slowing and loss of concentration, pessimistic worry, agitation, and self-deprecation. Physical changes also occur, especially in severe or "melancholic" depression. These include insomnia or hypersomnia, anorexia and weight loss (or sometimes overeating), decreased energy and libido, and disruption of normal circadian rhythms of activity, body temperature, and many endocrine functions.

Treatment regimens commonly include the use of tricyclic antidepressants, monoamine oxidase inhibitors, some psychotropic drugs, lithium carbonate, and electroconvulsive therapy (ECT) (see R. J. Baldessarini in *Goodman & Gilman's The Pharmacological Basis of Therapeutics*, 9th Edition, Chapter 19, McGraw-Hill, 1996 for a review). More recently, new classes of antidepressant drugs are being developed including selective serotonin reuptake inhibitors (SSRIs), specific monoamine reuptake inhibitors and $5\text{-HT}_{1A}$ receptor agonists, antagonists and partial agonists.

Anxiety is an emotional condition characterised by feelings such as apprehension and fear accompanied by physical sympoms such as tachycardia, increased respiration, sweating and tremor. It is a normal emotion but when it is severe and disabling it becomes pathological.

Anxiety disorders are generally treated using benzodiazepine sedative-antianxiety agents. Potent benzodiazepines are effective in panic disorder as well as in generalised anxiety disorder, however, the risks associated with drug dependency may limit their long-term use. $5\text{-HT}_{1A}$ receptor partial agonists also have useful anxiolytic and other psychotropic activity, and less likelihood of sedation and dependance (see R. J. Baldessarini in *Goodman & Gilman's The Pharmacological Basis of Therapeutics*, 9th Edition, Chapter 18, McGraw-Hill, 1996 for a review).

Neurokinin 1 (NK-1; substance P) receptor antagonists are being developed for the treatment of a number of physiological disorders associated with an excess or imbalance of tachykinins, and in particular substance P. Examples of such conditions include disorders of the central nervous system such as anxiety, depression and psychosis (see, for instance, International (PCT) patent specification Nos. WO 95/16679, WO 95/18124 and WO 95/23798).

It might therefore be desirable to investigate the treatment of depression and/or anxiety using a combination of a tachykinin antagonist and an antidepressant and/or an anti-anxiety agent. Indeed, such a desideratum has already been considered in International (PCT) patent specification No. WO 96/24353 (published Aug. 15th, 1996) which claims methods for the treatment of psychiatric disorders using a combination of a tachykinin antagonist and a serotonin agonist or selective serotonin reuptake inhibitor. However, the disclosure of WO 96/24353 does not provide any teaching as to whether the claimed combination has any efficacy and in particular there is no direction towards specific combinations which might potentiate the antidepressant or anxiolytic effects of the individual therapeutic agents. There is no clear direction from WO 96/24353 to which class of tachykinin antagonist (e.g. NK-1, NK-2 or NK-3 receptor antagonists) would be of use in the claimed combinations, nor how a person of ordinary skill in the art might identify suitable compounds for use in combination with a serotonin agonist or a selective serotonin reuptake inhibitor. Furthermore, there is no teaching which would enable a person of ordinary skill in the art to identify those compounds with sustained activity following oral administration for use in the claimed combinations. At best, WO 96/24353 merely recites in one document that which was already recognised in the art, namely that tachykinin antagonists might be of use in the treatment of psychiatric disorders and that serotonin agonists and selective serotonin reuptake inhibitors are effective in the treatment of psychiatric disorders.

There therefore remains a need for an effective combination of an antidepressant and/or an anti-anxiety agent with a NK-1 receptor antagonist, which combination provides an unexpected and advantageous antidepressant or anxiolytic effect. Such combinations may for example provide an enhanced antidepressant or anxiolytic effect. They may also provide for a rapid onset of action to combat depression and/or anxiety thereby enabling prescription on an "as-needed" basis.

CNS-penetrant NK-1 receptor antagonists have been found to provide an unexpected effect relevant to the treatment and prevention of depression and/or anxiety when used in combination with an antidepressant or anti-anxiety agent. While not being bound to any particular theory of operation, an enhanced effect at treating or preventing a psychological stress response in an animal assay is observed with the combination of drugs than would be expected from either drug alone. In particular, combination therapy of a CNS-penetrant NK-1 receptor antagonist selected from the compounds of formulae (I), (II), (III), (IV) and (V), and a selective serotonin reuptake inhibitor or a $5\text{-HT}_{1A}$ receptor agonist or antagonist effectively inhibits separation-induced vocalisations in guinea-pig pups. This is indicative of efficacy in the treatment of depression and/or anxiety. Such unexpected results would not have been predicted based on the disclosures in the art.

DETAILED DESCRIPTION OF THE DRAWING

A more complete understanding of the present invention may be obtained by reading the following description in conjunction with the appended figures.

Figure 1:
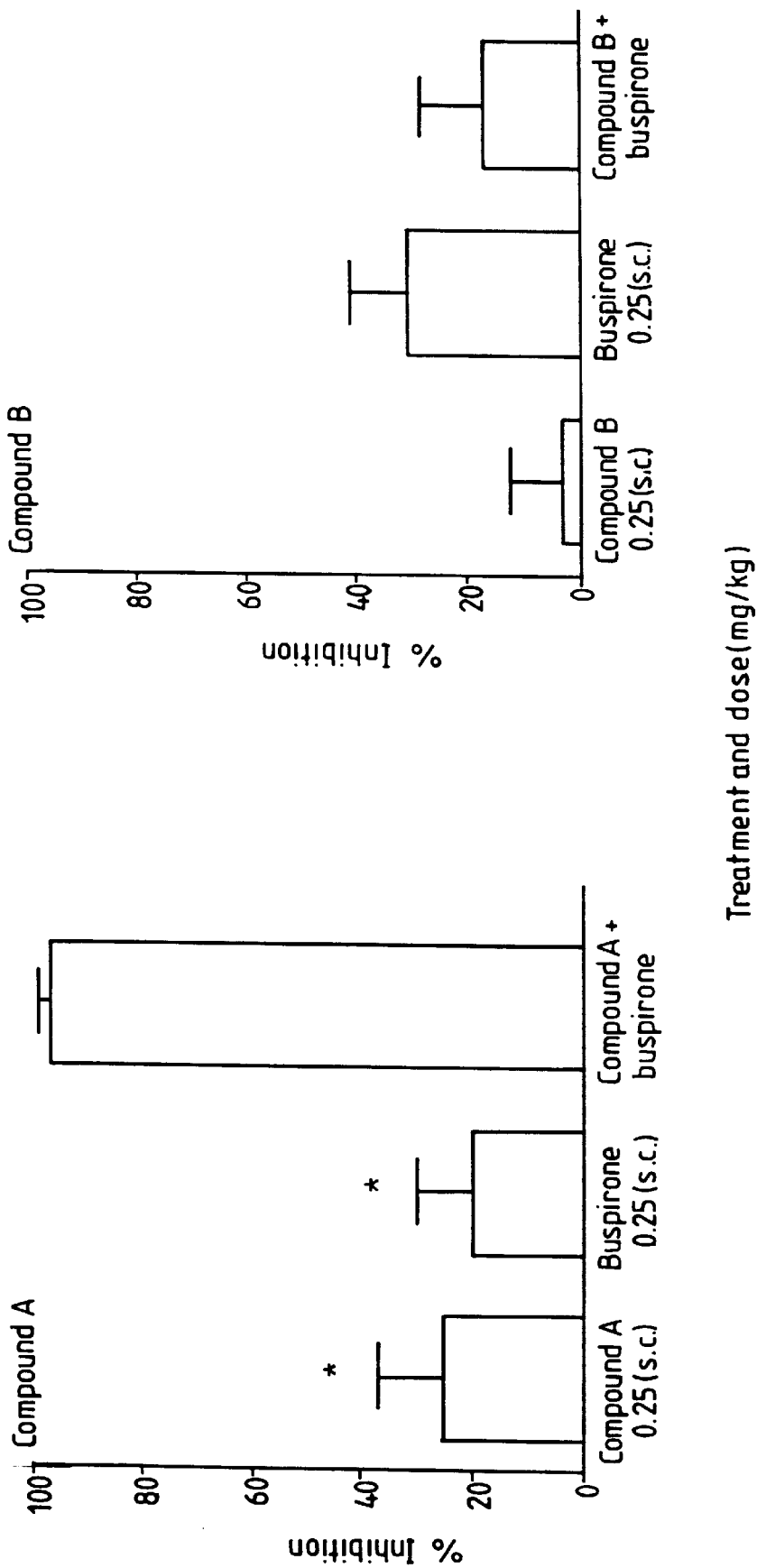

FIG. 1 depicts a summary of the data from a test of combinations of a CNS-penetrant NK-1 receptor antagonist with the anti-anxiety agent, buspirone, in a guinea-pig vocalisation assay. As further described herein, administration of the highly CNS penetrant NK-1 receptor antagonist Test Compound A (0.25 mg/kg s.c.), or buspirone (0.25 mg/kg s.c.) alone attenuated separation-induced vocalisations by approximately 25% compared with the baseline vocalisation response determined using the same animals on the previous day. Combined administration of Test Compound A (0.25 mg/kg s.c.) with buspirone (0.25 mg/kg s.c.) virtually abolished separation-induced vocalisations. The NK-1 receptor specificity of this effect was confirmed by the failure of the less active enantiomer, Test Compound B (0.25 mg/kg s.c.) to attenuate separation-induced vocalisations when administered alone, or to potentiate the inhibitory effect of buspirone (0.25 mg/kg s.c.).

Figure 2:
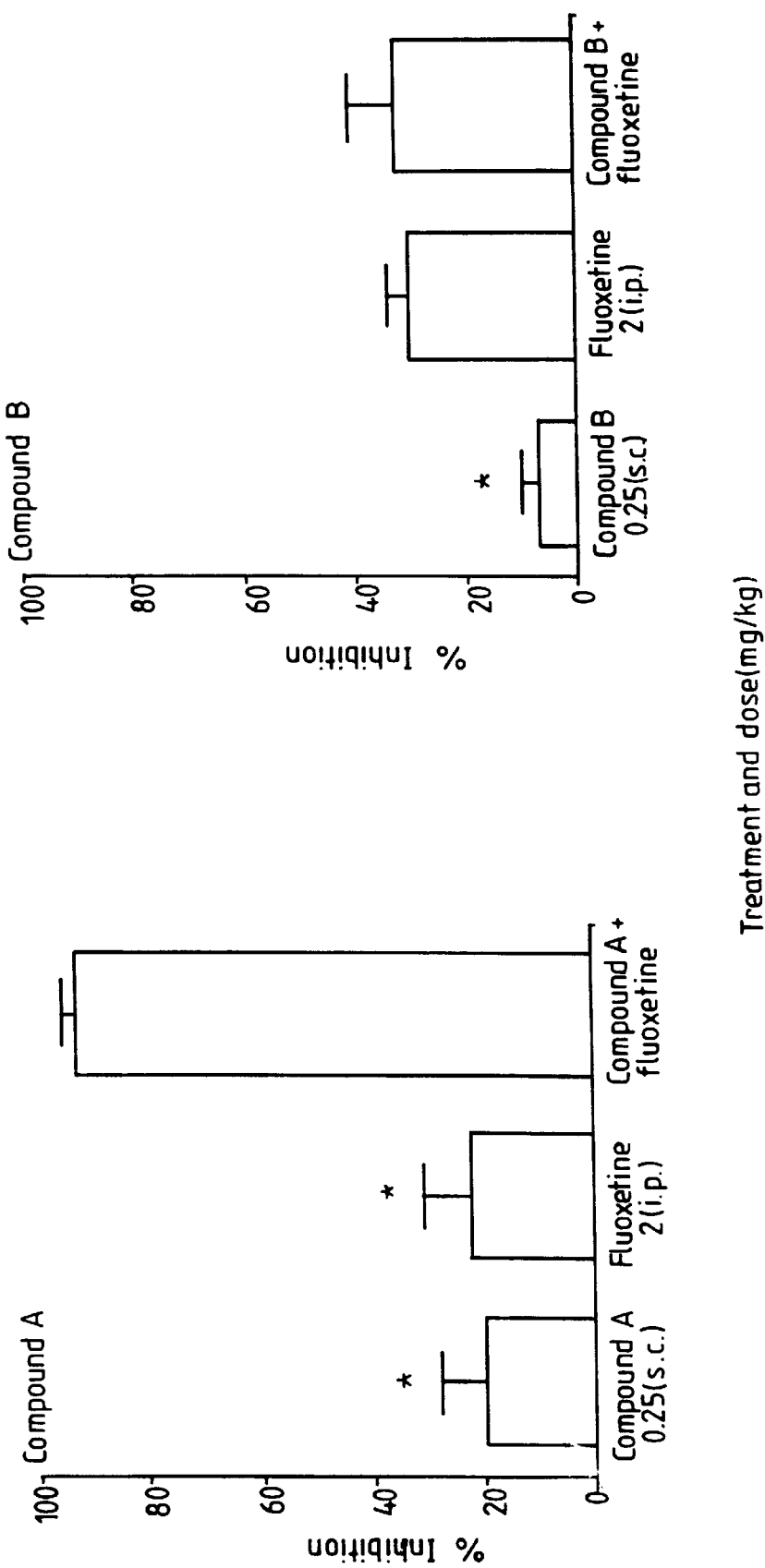

FIG. 2 depicts a summary of the data from a test of combinations of a CNS-penetrant NK-1 receptor antagonist with the antidepressant agent, fluoxetine, in a guinea-pig vocalisation assay. As further described herein, administration of the highly CNS penetrant NK-1 receptor antagonist Test Compound A (0.25 mg/kg s.c.), or fluoxetine (2 mg/kg i.p.) alone attenuated separation-induced vocalisations by approximately 25% compared with the baseline vocalisation response determined using the same animals on the previous day. Combined administration of Test Compound A (0.25 mg/kg s.c.) with fluoxetine (2 mg/kg i.p.) virtually abolished separation-induced vocalisations. The NK-1 receptor specificity of this effect was confirmed by the failure of the less active enantiomer, Test Compound B (0.25 mg/kg s.c.) to attenuate separation-induced vocalisations when administered alone, or to potentiate the inhibitory effect of fluoxetine (2 mg/kg i.p.).

The present invention accordingly provides the use of a CNS-penetrant NK-1 receptor antagonist and an antidepressant or anti-anxiety agent for the manufacture of a medicament for the treatment or prevention of depression and/or anxiety.

The present invention also provides a method for the treatment or prevention of depression and/or anxiety, which method comprises administration to a patient in need of such treatment an amount of a CNS-penetrant NK-1 receptor antagonist and an amount of an antidepressant or anti-anxiety agent, such that together they give effective relief.

In a further aspect of the present invention, there is provided a pharmaceutical composition comprising a CNS-penetrant NK-1 receptor antagonist and an antidepressant or anti-anxiety agent, together with at least one pharmaceutically acceptable carrier or excipient.

It will be appreciated that the CNS-penetrant NK-1 receptor antagonist and antidepressant or anti-anxiety agent may be present as a combined preparation for simultaneous, separate or sequential use for the treatment or prevention of depression and/or anxiety. Such combined preparations may be, for example, in the form of a twin pack.

In a further or alternative aspect of the present invention, there is therefore provided a product comprising a CNS-penetrant NK-1 receptor antagonist and an antidepressant or anti-anxiety agent as a combined preparation for simultaneous, separate or sequential use in the treatment or prevention of depression and/or anxiety.

It will be appreciated that when using a combination of the present invention, both the CNS-penetrant NK-1 receptor antagonist and the antidepressant or anti-anxiety agent will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially. Therefore, by way of example, the antidepressant or anti-anxiety agent may be administered as a tablet and then, within a reasonable period of time, the CNS-penetrant NK-1 receptor antagonist may be administered either as an oral dosage form such as a tablet or a fast-dissolving oral dosage form. By a "fast dissolving oral formulation" is meant, an oral delivery form which when placed on the tongue of a patient, dissolves within about 10 seconds.

By "reasonable period of time" is meant a time period that is not in excess of about 1 hour. That is, for example, if the antidepressant or antianxiety agent is provided as a tablet, then within one hour, the CNS-penetrant NK-1 receptor antagonist should be administered, either in the same type of dosage form, or another dosage form which provides effective delivery of the medicament.

The compositions of the present invention are useful for the treatment of depression. As used herein, the term "depression" includes depressive disorders, for example, single episodic or recurrent major depressive disorders, and dysthymic disorders, depressive neurosis, and neurotic depression; melancholic depression including anorexia, weight loss, insomnia and early morning waking, and psychomotor retardation; atypical depression (or reactive depression) including increased appetite, hypersomnia, psychomotor agitation or irritability, anxiety and phobias; seasonal affective disorder; or bipolar disorders or manic depression, for example, bipolar I disorder, bipolar II disorder and cyclothymic disorder.

Other mood disorders encompassed within the term "depression" include dysthymic disorder with early or late onset and with or without atypical features; dementia of the Alzheimer's type, with early or late onset, with depressed mood; vascular dementia with depressed mood; mood disorders induced by alcohol, amphetamines, cocaine, hallucinogens, inhalants, opioids, phencyclidine, sedatives, hypnotics, anxiolytics and other substances; schizoaffective disorder of the depressed type; and adjustment disorder with depressed mood.

The compositions of the present invention are useful for the treatment of anxiety. As used herein, the term "anxiety" includes anxiety disorders, such as panic disorder with or without agoraphobia, agoraphobia without history of panic disorder, specific phobias, for example, specific animal phobias, social phobias, obsessive-compulsive disorder, stress disorders including post-traumatic stress disorder and acute stress disorder, and generalised anxiety disorders.

"Generalised anxiety" is typically defined as an extended period (e.g. at least six months) of excessive anxiety or worry with symptoms on most days of that period. The anxiety and worry is difficult to control and may be accompanied by restlessness, being easily fatigued, difficulty concentrating, irritability, muscle tension, and disturbed sleep.

"Panic disorder" is defined as the presence of recurrent panic attacks followed by at least one month of persistent concern about having another panic attack. A "panic attack" is a discrete period in which there is a sudden onset of intense apprehension, fearfulness or terror. During a panic attack, the individual may experience a variety of symptoms including palpitations, sweating, trembling, shortness of breath, chest pain, nausea and dizziness. Panic disorder may occur with or without agoraphobia.

"Phobias" includes agoraphobia, specific phobias and social phobias. "Agoraphobia" is characterised by an anxiety about being in places or situations from which escape might be difficult or embarrassing or in which help may not be available in the event of a panic attack. Agoraphobia may occur without history of a panic attack. A "specific phobia" is characterised by clinically significant anxiety provoked by exposure to a specific feared object or situation. Specific phobias include the following subtypes: animal type, cued by animals or insects; natural environment type, cued by objects in the natural environment, for example storms, heights or water; blood-injection-injury type, cued by the sight of blood or an injury or by seeing or receiving an injection or other invasive medical procedure; situational type, cued by a specific situation such as public transportation, tunnels, bridges, elevators, flying, driving or enclosed spaces; and other type where fear is cued by other stimuli. Specific phobias may also be referred to as simple phobias. A "social phobia" is characterised by clinically significant anxiety provoked by exposure to certain types of social or performance circumstances. Social phobia may also be referred to as social anxiety disorder.

Other anxiety disorders encompassed within the term "anxiety" include anxiety disorders induced by alcohol, amphetamines, caffeine, cannabis, cocaine, hallucinogens, inhalants, phencyclidine, sedatives, hypnotics, anxiolytics and other substances, and adjustment disorders with anxiety or with mixed anxiety and depression.

Anxiety may be present with or without other disorders such as depression in mixed anxiety and depressive disorders. The compositions of the present invention are therefore useful in the treatment of anxiety with or without accompanying depression.

The compositions of the present invention are especially useful for the treatment of or prevention of depression and/or anxiety where the use of an antidepressant or antianxiety agent is generally prescribed. By the use of a combination of a CNS-penetrant NK-1 receptor antagonist and an antidepressant or anti-anxiety agent in accordance with the present invention, it is now also possible to treat or prevent depression and/or anxiety in patients for whom conventional antidepressant or anti-anxiety therapy might not be wholly successful or where dependance upon the antidepressant or anti-anxiety therapy is prevalent.

Suitable classes of antidepressant agent of use in the present invention include norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists and atypical antidepressants.

Another class of antidepressant agent of use in the present invention are noradrenergic and specific serotonergic antidepressants (NaSSAs). A suitable example of a NaSSA is mirtazapine.

Suitable norepinephrine reuptake inhibitors of use in the present invention include tertiary amine tricyclics and secondary amine tricyclics. Suitable examples of tertiary amine tricyclics include: amitriptyline, clomipramine, doxepin, imipramine and trimipramine, and pharmaceutically acceptable salts thereof Suitable examples of secondary amine tricyclics include: amoxapine, desipramine, maprotiline, nortriptyline and protriptyline, and pharmaceutically acceptable salts thereof.

Another norepinephrine reuptake inhibitor of use in the present invention is reboxetine.

Suitable selective serotonin reuptake inhibitors of use in the present invention include: fluoxetine, fluvoxamine, paroxetine and sertraline, and pharmaceutically acceptable salts thereof.

Suitable monoamine oxidase inhibitors of use in the present invention include: isocarboxazid, phenelzine, tranylcypromine and selegiline, and pharmaceutically acceptable salts thereof.

Suitable reversible inhibitors of monoamine oxidase of use in the present invention include: moclobemide, and pharmaceutically acceptable salts thereof.

Suitable serotonin and noradrenaline reuptake inhibitors of use in the present invention include: venlafaxine, and pharmaceutically acceptable salts thereof.

Suitable CRF antagonists of use in the present invention include those compounds described in International Patent Specification Nos. WO 94/13643, WO 94/13644, WO 94/13661, WO 94/13676 and WO 94/13677.

Suitable atypical antidepressants of use in the present invention include: bupropion, lithium, nefazodone, trazodone and viloxazine, and pharmaceutically acceptable salts thereof. Another suitable atypical antidepressant is sibutramine.

Other antidepressants of use in the present invention include adinazolam, alaproclate, amineptine, amitriptyline/ chlordiazepoxide combination, atipamezole, azamianserin, bazinaprine, befuraline, bifemelane, binodaline, bipenamol, brofaromine bupropion, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, litoxetine, lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, ritanserin, rolipram, sercloremine, setiptiline, sibutramine, sulbutiamine, sulpiride, tenilaxazine, thozalinone, thymoliberin, tianeptine, tiflucarbine, tofenacin, tofisopam, toloxatone, tomoxetine, veralipride, viqualine, zimelidine and zometapine, and pharmaceutically acceptable salts thereof, and St. John's wort herb, or *Hypericum perforatum*, or extracts thereof Suitable classes of anti-anxiety agent of use in the present invention include benzodiazepines and 5-HT$_{1A}$ agonists or antagonists, especially 5-HT$_{1A}$ partial agonists, and corticotropin releasing factor (CRF) antagonists. In addition to benzodiazepines, other suitable classes of anti-anxiety agent are nonbenzodiazepine sedative-hypnotic drugs such as zolpidem; mood-stabilizing drugs such as clobazam, gabapentin, lamotrigine, loreclezole, oxcarbamazepine, stiripentol and vigabatrin; and barbiturates.

Suitable benzodiazepines of use in the present invention include: alprazolam, chlordiazepoxide, clonazepam, chlorazepate, diazepam, halazepam, lorazepam, oxazepam and prazepam, and pharmaceutically acceptable salts thereof.

Suitable 5-HT$_{1A}$ receptor agonists or antagonists of use in the present invention include, in particular, the 5-HT$_{1A}$ receptor partial agonists buspirone, flesinoxan, gepirone and ipsapirone, and pharmaceutically acceptable salts thereof An example of a compound with 5-HT$_{1A}$ receptor antagonist/ partial agonist activity is pindolol.

Suitable CRF antagonists of use in the present invention include those compounds described in International Patent Specification Nos. WO 94/13643, WO 94/13644, WO 94/13661, WO 94/13676 and WO 94/13677.

Another class of anti-anxiety agent of use in the present invention are compounds having muscarinic cholinergic activity. Suitable compounds in this class include m1 muscarinic cholinergic receptor agonists such as those compounds described in European Patent Specification Nos. 0 709 093, 0 709 094 and 0 773 021, and International patent Specification No. WO 96/12711.

Another class of anti-anxiety agent of use in the present invention are compounds acting on ion channels. Suitable compounds in this class include carbamazepine, lamotrigine and valproate, and pharmaceutically acceptable salts thereof.

Particularly preferred CNS-penetrant NK-1 receptor antagonists are those described in European Patent Specification No. 0 577 394, i.e. compounds of formula (I):

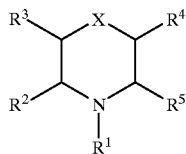
(I)

or a pharmaceutically acceptable salt thereof, wherein:
$R^1$ is selected from the group consisting of:
(1) hydrogen;
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$NR^9R^{10}$, wherein $R^9$ and $R^{10}$ are independently selected from:
    (i) hydrogen,
    (ii) $C_{1-6}$alkyl,
    (iii) hydroxy-$C_{1-6}$alkyl, and
    (iv) phenyl,
  (i) —$NR^9COR^{10}$, wherein $R^9$ and $R^{10}$ are as defined above,
  (j) —$NR^9CO_2R^{10}$, wherein $R^9$ and $R^{10}$ are as defined above,
  (k) —$CONR^9R^{10}$, wherein $R^9$ and $R^{10}$ are as defined above,
  (l) —$COR^9$, wherein $R^9$ is as defined above,
  (m) —$CO_2R^9$, wherein $R^9$ is as defined above,
  (n) heterocycle, wherein the heterocycle is selected from the group consisting of:
    (A) benzimidazolyl,
    (B) benzofuranyl,
    (C) benzthiophenyl,
    (D) benzoxazolyl,
    (E) furanyl,
    (F) imidazolyl,
    (G) indolyl,
    (H) isoxazolyl,
    (I) isothiazolyl,
    (J) oxadiazolyl,
    (K) oxazolyl,
    (L) pyrazinyl,
    (M) pyrazolyl,
    (N) pyridyl,
    (O) pyrimidyl,
    (P) pyrrolyl,
    (Q) quinolyl,
    (R) tetrazolyl,
    (S) thiadiazolyl,
    (T) thiazolyl,
    (U) thienyl,
    (V) triazolyl,
    (W) azetidinyl,
    (X) 1,4-dioxanyl,
    (Y) hexahydroazepinyl,
    (Z) oxanyl,
    (AA) piperazinyl,
    (AB) piperidinyl,
    (AC) pyrrolidinyl,
    (AD) tetrahydrofuranyl, and
    (AE) tetrahydrothienyl,
    and wherein the heterocylcle is unsubstituted or substituted with one or more substituent(s) selected from:
      (i) $C_{1-6}$alkyl, unsubstituted or substituted with halo, —$CF_3$, —$OCH_3$, or phenyl,
      (ii) $C_{1-6}$alkoxy,
      (iii) oxo,
      (iv) hydroxy,
      (v) thioxo,
      (vi) —$SR^9$, wherein $R^9$ is as defined above,
      (vii) halo,
      (viii) cyano,
      (ix) phenyl,
      (x) trifluoromethyl,
      (xi) —$(CH_2)_m$—$NR^9R^{10}$, wherein m is 0, 1 or 2, and $R^9$ and $R^{10}$ are as defined above,
      (xii) —$NR^9COR^{10}$, wherein $R^9$ and $R^{10}$ are as defined above,
      (xiii) —$CONR^9R^{10}$, wherein $R^9$ and $R^{10}$ are as defined above,
      (xiv) —$CO_2R^9$, wherein $R^9$ is as defined above, and
      (xv) —$(CH_2)_m$—$OR^9$, wherein m and $R^9$ are as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$CONR^9R^{10}$, wherein $R^9$ and $R^{10}$ are as defined above,
  (i) —$COR^9$, wherein $R^9$ is as defined above,
  (j) —$CO_2R^9$, wherein $R^9$ is as defined above,
  (k) heterocycle, wherein the heterocycle is as defined above;
(4) $C_{2-6}$alkynyl;
(5) phenyl, unsubstitued or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo,
  (f) —CN,
  (g) —$NO_2$,
  (h) —$CF_3$,
  (i) —$(CH_2)_m$—$NR^9R^{10}$, wherein m, $R^9$ and $R^{10}$ are as defined above,
  (j) —$NR^9COR^{10}$, wherein $R^9$ and $R^{10}$ are as defined above,
  (k) —$NR^9CO_2R^{10}$, wherein $R^9$ and $R^{10}$ are as defined above,
  (l) —$CONR^9R^{10}$, wherein $R^9$ and $R^{10}$ are as defined above, (m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;

$R^2$ and $R^3$ are independently selected from the group consisting of:
(1) hydrogen;
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$NR^9R^{10}$, wherein $R^9$ and $R^{10}$ are independently selected from:
    (i) —$NR^9COR^{10}$, wherein $R^9$ and $R^{10}$ are as defined above,
    (j) —$NR^9CO_2R^{10}$, wherein $R^9$ and $R^{10}$ are as defined above,
    (k) —$CONR^9R^{10}$, wherein $R^9$ and $R^{10}$ are as defined above,
    (l) —$COR^9$, wherein $R^9$ is as defined above, and
    (m) —$CO_2R^9$, wherein $R^9$ is as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$CONR^9R^{10}$ wherein $R^9$ and $R^{10}$ are as defined above,
  (i) —$COR^9$, wherein $R^9$ is as defined above,
  (j) —$CO_2R^9$, wherein $R^9$ is as defined above;
(4) $C_{2-6}$alkynyl;
(5) phenyl, unsubstituted or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo,
  (f) —CN,
  (g) —$NO_2$,
  (h) —$CF_3$,
  (i) —$(CH_2)_m$—$NR^9R^{10}$, wherein m, $R^9$ and $R^{10}$ are as defined above,
  (j) —$NR^9COR^{10}$, wherein $R^9$ and $R^{10}$ are as defined above,
  (k) —$NR^9CO_2R^{10}$, wherein $R^9$ and $R^{10}$ are as defined above,
  (l) —$CONR^9R^{10}$, wherein $R^9$ and $R^{10}$ are as defined above,
  (m) —$CO_2NR^9R^{10}$, wherein $R^9$ and $R^{10}$ are as defined above,
  (n) —$COR^9$, wherein $R^9$ is as defined above,
  (o) —$CO_2R^9$, wherein $R^9$ is as defined above;

and the groups $R^1$ and $R^2$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;

and the groups $R^2$ and $R^3$ may be joined together to form a carbocyclic ring selected from the group consisting of:
(a) cyclopentyl,
(b) cyclohexyl,
(c) phenyl, and wherein the carbocyclic ring is unsubstituted or substituted with one or more substituents selected from:
(i) $C_{1-6}$alkyl,
(ii) $C_{1-6}$alkoxy,
(iii) —$NR^9R^{10}$, wherein $R^9$ and $R^{10}$ are as defined above,
(iv) halo, and
(v) trifluoromethyl;

and the groups $R^2$ and $R^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl, and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;

is selected from the group consisting of:
(1) —O—,
(2) —S—,
(3) —SO—, and
(4) —$SO_2$—;

$R^4$ is selected from the group consisting of:

(1)

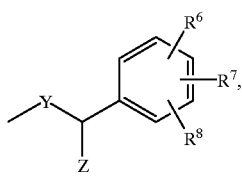

(2) —Y-$C_{1-8}$alkyl, wherein alkyl is unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;
(3) —Y-$C_{2-6}$alkenyl, wherein the alkenyl is unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above,
(4) —O(CO)-phenyl, wherein the phenyl is unsubstituted or substituted with one or more of $R^6$, $R^7$ and $R^8$;

$R^5$ is selected from the group consisting of:
(1) phenyl, unsubstituted or substituted with one or more of $R^{11}$, $R^{12}$ and $R^{13}$;
(2) $C_{1-8}$alkyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above;
(4) heterocycle, wherein the heterocycle is as defined above;

$R^6$, $R^7$ and $R^8$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$ wherein $R^9$ and $R^{10}$ are as defined above,
(i) —$COR^9$ wherein $R^9$ is as defined above,
(j) —$CO_2R^9$, wherein $R^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above, (k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above;
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or C$_{1-5}$alkyl.
(11) —SOR$^{14}$, wherein R$^{14}$ is as defined above,
(12) —SO$_2$R$^{14}$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,
(15) NR$^9$R$^{10}$, wherein R$^9$ and R$^{10}$ are as defined above,
(16) NR$^9$CO$_2$R$^{10}$, wherein R$^9$ and R$^{10}$ are as defined above,
(17) hydroxy,
(18) C$_{1-6}$alkoxy,
(19) COR$^9$, wherein R$^9$ is as defined above,
(20) CO$_2$R$^9$, wherein R$^9$ is as defined above,
R$^{11}$, R$^{12}$ and R$^{13}$ are independently selected from the definitions of R$^6$, R$^7$ and R$^8$, or —OX;
Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein R$^{15}$ and R$^{16}$ are independently selected from the group consisting of:
(a) C$_{1-6}$alkyl, unsubstituted or substituted with one or more of the substituents selected from:
(i) hydroxy,
(ii) oxo,
(iii) C$_{1-6}$alkoxy,
(iv) phenyl-C$_{1-3}$alkoxy,
(v) phenyl,
(vi) —CN,
(vii) halo,
(viii) —NR$^9$R$^{10}$, wherein R$^9$ and R$^{10}$ are as defined above,
(ix) —NR$^9$COR$^{10}$, wherein R$^9$ and R$^{10}$ are as defined above,
(x) —NR$^9$CO$_2$R$^{10}$, wherein R$^9$ and R$^{10}$ are as defined above,
(xi) —CONR$^9$R$^{10}$, wherein R$^9$ and R$^{10}$ are as defined above,
(xii) —COR$^9$, wherein R$^9$ is as defined above, and
(xiii) —CO$_2$R$^9$, wherein R$^9$ is as defined above;
(b) phenyl, unsubstituted or substituted with one or more of the substituent(s) selected from:
(i) hydroxy,
(ii) C$_{1-6}$alkoxy,
(iii) C$_{1-6}$alkyl,
(iv) C$_{2-5}$alkenyl,
(v) halo,
(vi) —CN,
(vii) —NO$_2$,
(viii) —CF$_3$,
(ix) —(CH$_2$)$_m$—NR$^9$R$^{10}$, wherein m, R$^9$ and R$^{10}$ are as defined above,
(x) —NR$^9$COR$^{10}$, wherein R$^9$ and R$^{10}$ are as defined above,
(xi) —NR$^9$CO$_2$R$^{10}$, wherein R$^9$ and R$^{10}$ are as defined above,
(xii) —CONR$^9$R$^{10}$, wherein R$^9$ and R$^{10}$ are as defined above,
(xiii) —CO$_2$NR$^9$R$^{10}$, wherein R$^9$ and R$^{10}$ are as defined above,
(xiv) —COR$^9$, wherein R$^9$ is as defined above, and
(xv) —CO$_2$R$^9$, wherein R$^9$ is as defined above;
Z is selected from:
(1) hydrogen,
(2) C$_{1-4}$alkyl, and
(3) hydroxy, with the proviso that if Y is —O—, Z is other than hydroxy, or if Y is —CHR$^{15}$—, then Z and R$^{15}$ may be joined together to form a double bond.

Particularly preferred compounds of formula (I) are those wherein: R$^1$ is selected from the group consisting of:
(1) C$_{1-6}$alkyl, substituted with one or more of the substituents selected from:
(a) heterocycle, wherein the heterocycle is selected from the group consisting of:
(A) benzimidazolyl,
(B) imidazolyl,
(C) isoxazolyl,
(D) isothiazolyl,
(E) oxadiazolyl,
(F) pyrazinyl,
(G) pyrazolyl,
(H) pyridyl,
(I) pyrrolyl,
(J) tetrazolyl,
(K) thiadiazolyl,
(L) triazolyl, and
(M) piperidinyl,
and wherein the heterocycle is unsubstituted or substituted with one or more substituent(s) selected from:
(i) C$_{1-6}$alkyl, unsubstituted or substituted with halo, —CF$_3$, —OCH$_3$, or phenyl,
(ii) C$_{1-6}$alkoxy,
(iii) oxo,
(iv) thioxo,
(v) cyano,
(vi) —SCH$_3$,
(vii) phenyl,
(viii) hydroxy,
(ix) trifluoromethyl,
(x) —(CH$_2$)$_m$—NR$^9$R$^{10}$, wherein m is 0, 1 or 2, and R$^9$ and R$^{10}$ are independently selected from:
(I) hydrogen,
(II) C$_{1-6}$alkyl,
(III) hydroxyC$_{1-6}$alkyl, and
(IV) phenyl,
(xi) —NR$^9$COR$^{10}$, wherein R$^9$ and R$^{10}$ are as defined above, and
(xii) —CONR$^9$R$^{10}$, wherein R$^9$ and R$^{10}$ are as defined above,
R$^2$ and R$^3$ are independently selected from the group consisting of:
(1) hydrogen;
(2) C$_{1-6}$alkyl
(3) C$_{2-6}$alkenyl, and
(5) phenyl;

X is —O—;
R$^4$ is

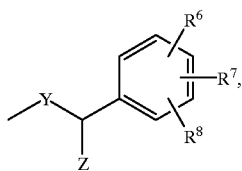

R$^5$ is phenyl, unsubstituted or substituted with halo;
R$^6$, R$^7$ and R$^8$ are independently selected from the group consisting of:
(1) hydrogen,
(2) C$_{1-6}$alkyl,
(3) halo, and
(4) —CF$_3$;
Y is —O—; and
Z is hydrogen or C$_{1-4}$alkyl;
and pharmaceutically acceptable salts thereof.

A particularly preferred compound of formula (I) is 2-(R)-(1-(R)-(3,5-bis(trifluoromethyl)pheny)lethoxy)-3-(S)-(4-fluorophenyl)- 4-(3-(5-oxo-1H,4H-1,2,4-triazolo) methyl)morpholine; or a pharmaceutically acceptable salt thereof.

Further preferred CNS-penetrant NK-1 receptor antagonists are those described in International (PCT) Patent Specification No. WO 95/18124, i.e. compounds of formula (II):

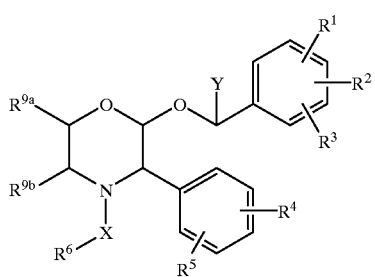

or a pharmaceutically acceptable salt or prodrug thereof, wherein
R$^1$ is hydrogen, halogen, C$_{1-6}$alkyl, C$_{1-6}$alkoxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;
R$^2$ is hydrogen, halogen, C$_{1-6}$alkyl, C$_{1-6}$alkoxy substituted by C$_{1-4}$alkoxy or CF$_3$;
R$^3$ is hydrogen, halogen or CF$_3$;
R$^4$ is hydrogen, halogen, C$_{1-6}$alkyl, C$_{1-6}$alkoxy, CF$_3$, NO$_2$, CN, SR$^a$, SOR$^a$, SO$_2$R$^a$, CO$_2$R$^a$, CONR$^a$R$^b$, C$_{2-6}$alkenyl, C$_{2-6}$alkynyl or C$_{1-4}$alkyl substituted by C$_{1-4}$alkoxy, where R$^a$ and R$^b$ each independently represent hydrogen or C$_{1-4}$alkyl;
R$^5$ is hydrogen, halogen, C$_{1-6}$alkyl, C$_{1-6}$alkoxy substituted by C$_{1-4}$alkoxy or CF$_3$;
R$^6$ is a 5-membered or 6-membered heterocyclic ring containing 2 or 3 nitrogen atoms optionally substituted by =O, =S or a C$_{1-4}$alkyl group, and optionally substituted by a group of the formula ZNR$^7$R$^8$ where Z is C$_{1-6}$alkylene or C$_{3-6}$cycloalkylene;
R$^7$ is hydrogen, C$_{1-4}$alkyl, C$_{3-7}$cycloalkyl or C$_{3-7}$cycloalkylC$_{1-4}$alkyl, or C$_{2-4}$alkyl substituted by C$_{1-4}$alkoxy or hydroxyl;
R$^8$ is hydrogen, C$_{1-4}$alkyl, C$_{3-7}$cycloalkyl or C$_{3-7}$cycloalkylC$_{1-4}$alkyl, or C$_{2-4}$alkyl substituted by one or two substituents selected from C$_{1-4}$alkoxy, hydroxyl or a 4, 5 or 6 membered heteroaliphatic ring containing one or two heteroatoms selected from N, O and S;
or R$^7$, R$^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is C$_{1-4}$alkyl optionally substituted by hydroxy or C$_{1-4}$alkoxy;
or R$^7$, R$^8$ and the nitrogen atom to which they are attached form a non-aromatic azabicyclic ring system of 6 to 12 ring atoms;
or Z, R$^7$ and the nitrogen atom to which they are attached form a heteroaliphatic ring of 4 to 7 ring atoms which may optionally contain an oxygen ring atom;
R$^{9a}$ and R$^{9b}$ are each independently hydrogen or C$_{1-4}$alkyl, or R$^{9a}$ and R$^{9b}$ are joined so, together with the carbon atoms to which they are attached, there is formed a C$_{5-7}$ ring;
X is an alkylene chain of 1 to 4 carbon atoms optionally substituted by oxo; and
Y is a C$_{1-4}$alkyl group optionally substituted by a hydroxyl group;
with the proviso that if Y is C$_{1-4}$alkyl, R$^6$ is susbstituted at least by a group of formula ZNR$^7$R$^8$ as defined above.

Particularly preferred compounds of formula (II) are those of formula (IIa) and pharmaceutically acceptable salts thereof:

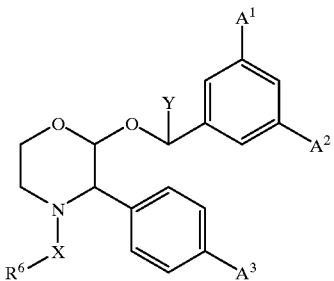

wherein:
A$^1$ is fluorine or CF$_3$;
A$^2$ is fluorine or CF$_3$;
A$^3$ is fluorine or hydrogen;
and X, Y and R$^6$ are as defined in relation to formula (II).

Particularly preferred compounds of formula (II) include: 2-(R)-(1-(R)-(3,5-bis(trifluoromethyl)phenyl)ethoxy)-4-(5-(dimethylamino) methyl-1,2,3-triazol-4-yl)methyl-3-(S)-phenylmorpholine; 2-(R)-(1-(R)-(3,5-bis(trifluoromethyl) phenyl)ethoxy)-4-(5-(dimethylamino) methyl-1,2,3-triazol-4-yl)methyl-3-(S)-(4-fluorophenyl)morpholine; and pharmaceutically acceptable salts thereof.

Further preferred CNS-penetrant NK-1 receptor antagonists are those described in European Patent Specification No. WO 95/23798, i.e. compounds of formula (III):

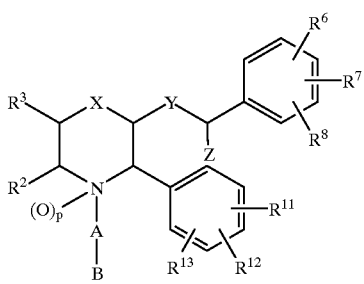

(III)

or a pharmaceutically acceptable salt thereof, wherein:
$R^2$ and $R^3$ are independently selected from the group consisting of:
(1) hydrogen,
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$NR^9R^{10}$, wherein $R^9$ and $R^{10}$ are independently selected from:
    (I) hydrogen,
    (ii) $C_{1-6}$alkyl,
    (iii) hydroxy-$C_{1-6}$alkyl, and
    (iv) phenyl,
  (i) —$NR^9COR^{10}$, wherein $R^9$ and $R^{10}$ are as defined above,
  (j) —$NR^9CO_2R^{10}$, wherein $R^9$ and $R^{10}$ are as defined above,
  (k) —$CONR^9R^{10}$, wherein $R^9$ and $R^{10}$ are as defined above,
  (l) —$COR^9$, wherein $R^9$ is as defined above, and
  (m) —$CO_2R^9$, wherein $R^9$ is as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$CONR^9R^{10}$ wherein $R^9$ and $R^{10}$ are as defined above,
  (i) —$COR^9$ wherein $R^9$ is as defined above,
  (j) —$CO_2R^9$, wherein $R^9$ is as defined above;
(4) $C_{2-6}$alkynyl;
(5) phenyl, unsubstituted or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo,
  (f) —CN,
  (g) —$NO_2$,
  (h) —$CF_3$,
  (i) —$(CH_2)_m$—$NR^9R^{10}$, wherein m, $R^9$ and $R^{10}$ are as defined above,
  (j) —$NR^9COR^{10}$, wherein $R^9$ and $R^{10}$ are as defined above,
  (k) $NR^9CO_2R^{10}$, wherein $R^9$ and $R^{10}$ are as defined above,
  (l) —$CONR^9R^{10}$, wherein $R^9$ and $R^{10}$ are as defined above,
  (m) —$CO_2NR^9R^{10}$, wherein $R^9$ and $R^{10}$ are as defined above,
  (n) —$COR^9$, wherein $R^9$ is as defined above,
  (o) —$CO_2R^9$, wherein $R^9$ is as defined above;
and the groups $R^2$ and $R^3$ may be joined together to form a carbocyclic ring selected from the group consisting of:
  (a) cyclopentyl,
  (b) cyclohexyl,
  (c) phenyl,
and wherein the carbocyclic ring is unsubstituted or substituted with one or more substituents selected from:
  (i) $C_{1-6}$alkyl,
  (ii) $C_{1-6}$alkoxy,
  (iii) —$NR^9R^{10}$, wherein $R^9$ and $R^{10}$ are as defined above,
  (iv) halo, and
  (v) trifluoromethyl;
and the groups $R^2$ and $R^3$ may be joined together to form a heterocyclic ring selected from the group consisting of:
  (a) pyrrolidinyl,
  (b) piperidinyl,
  (c) pyrrolyl,
  (d) pyridinyl,
  (e) imidazolyl,
  (f) furanyl,
  (g) oxazolyl,
  (h) thienyl, and
  (i) thiazolyl,
and wherein the heterocyclic ring is unsubstituted or substituted with one or more substituent(s) selected from:
  (i) $C_{1-6}$alkyl,
  (ii) oxo,
  (iii) $C_{1-6}$alkoxy,
  (iv) —$NR^9R^{10}$, wherein $R^9$ and $R^{10}$ are as defined above,
  (v) halo, and
  (vi) trifluoromethyl;
$R^6$, $R^7$ and $R^8$ are independently selected from the group consisting of:
(1) hydrogen;
(2) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —$NR^9R^{10}$, wherein $R^9$ and $R^{10}$ are as defined above,
  (i) —$NR^9COR^{10}$, wherein $R^9$ and $R^{10}$ are as defined above,
  (j) —$NR^9CO_2R^{10}$, wherein $R^9$ and $R^{10}$ are as defined above, (k) —CONR⁹R¹⁰, wherein R⁹ and R¹⁰ are as defined above,
(l) —COR⁹, wherein R⁹ is as defined above, and
(m) —CO₂R⁹, wherein R⁹ is as defined above;
(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —CONR⁹R¹⁰ wherein R⁹ and R¹⁰ are as defined above,
  (i) —COR⁹ wherein R⁹ is as defined above,
  (j) —CO2R⁹, wherein R⁹ is as defined above;
(4) $C_{2-6}$alkynyl;
(5) phenyl, unsubstituted or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo,
  (f) —CN,
  (g) —NO₂,
  (h) —CF₃,
  (i) —(CH₂)$_m$—NR⁹R¹⁰, wherein m, R⁹ and R¹⁰ are as defined above,
  (j) —NR⁹COR¹⁰, wherein R⁹ and R¹⁰ are as defined above,
  (k) —NR⁹CO₂R¹⁰, wherein R⁹ and R¹⁰ are as defined above,
  (l) —CONR⁹R¹⁰, wherein R⁹ and R¹⁰ are as defined above,
  (m) —CO₂NR⁹R¹⁰, wherein R⁹ and R¹⁰ are as defined above,
  (n) —COR⁹, wherein R⁹ is as defined above,
  (o) —CO₂R⁹, wherein R⁹ is as defined above;
(6) halo,
(7) —CN,
(8) —CF₃,
(9) —NO₂,
(10) —SR¹⁴, wherein R¹⁴ is hydrogen or $C_{1-5}$alkyl,
(11) —SOR¹⁴, wherein R¹⁴ is as defined above,
(12) —SO₂R¹⁴, wherein R¹⁴ is as defined above,
(13) NR⁹COR¹⁰, wherein R⁹ and R¹⁰ are as defined above,
(14) CONR⁹COR¹⁰, wherein R⁹ and R¹⁰ are as defined above,
(15) NR⁹R¹⁰, wherein R⁹ and R¹⁰ are as defined above,
(16) NR⁹CO₂R¹⁰, wherein R⁹ and R¹⁰ are as defined above,
(17) hydroxy,
(18) $C_{1-6}$alkoxy,
(19) COR⁹, wherein R⁹ is as defined above,
(20) CO₂R⁹, wherein R⁹ is as defined above,
(21) 2-pyridyl,
(22) 3-pyridyl,
(23) 4-pyridyl,
(24) 5-tetrazolyl,
(25) 2-oxazolyl, and
(26) 2-thiazolyl;
R¹¹, R¹² and R¹³ are independently selected from the definitions of R⁶, R⁷ and R⁸, or —OX;
A is selected from the group consisting of:

(1) $C_{1-6}$alkyl, unsubstituted or substituted with one or more of the substituents selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo, wherein halo is fluoro, chloro, bromo or iodo,
  (h) —NR⁹R¹⁰, wherein R⁹ and R¹⁰ are as defined above,
  (i) —NR⁹COR¹⁰, wherein R⁹ and R¹⁰ are as defined above,
  (j) —NR⁹CO₂R¹⁰, wherein R⁹ and R¹⁰ are as defined above,
  (k) —CONR⁹R¹⁰, wherein R⁹ and R¹⁰ are as defined above,
  (l) —COR⁹, wherein R⁹ is as defined above, and
  (m) —CO₂R⁹, wherein R⁹ is as defined above;
(2) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl-$C_{1-3}$alkoxy,
  (e) phenyl,
  (f) —CN,
  (g) halo,
  (h) —CONR⁹R¹⁰ wherein R⁹ and R¹⁰ are as defined above,
  (i) —COR⁹ wherein R⁹ is as defined above, and
  (j) —CO₂R⁹, wherein R⁹ is as defined above; and
(3) $C_{2-6}$alkynyl;
B is a heterocycle, wherein the heterocycle is selected from the group consisting of:

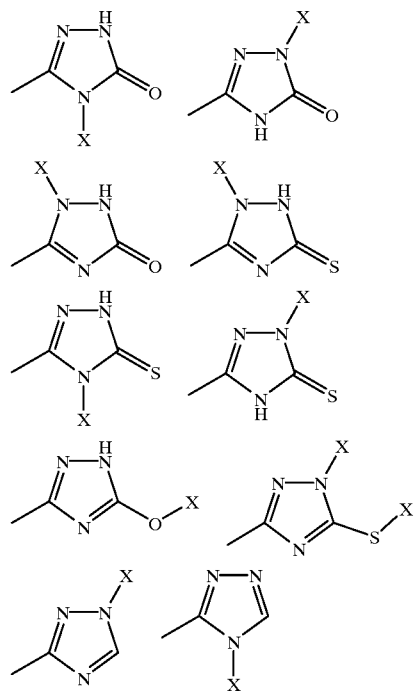

-continued

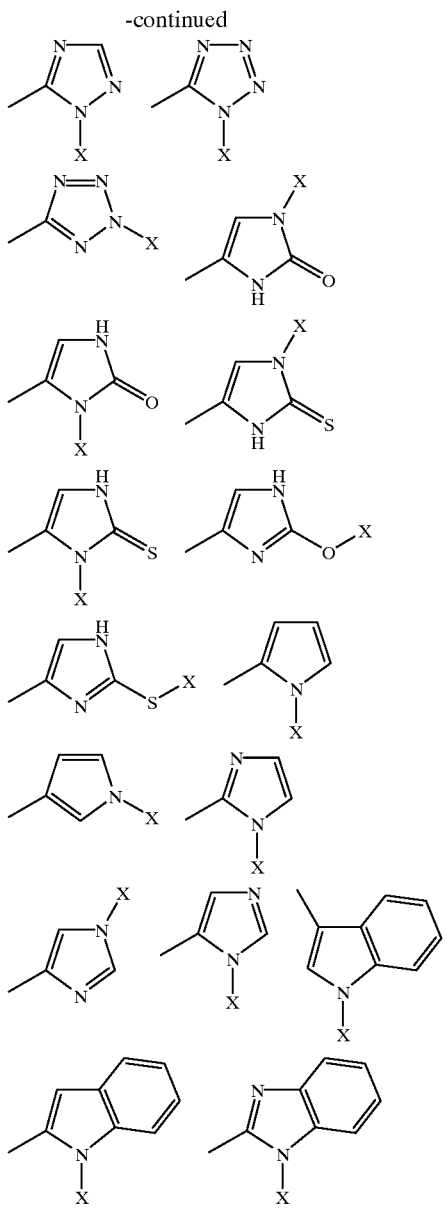

and wherein the heterocycle may be substituted in addition to —X with one or more substituent(s) selected from:
(i) $C_{1-6}$alkyl, unsubstituted or substituted with halo, —$CF_3$, —$OCH_3$, or phenyl,
(ii) $C_{1-6}$alkoxy,
(iii) oxo,
(iv) hydroxy,
(v) thioxo,
(vi) —$SR^9$, wherein $R^9$ is as defined above,
(vii) halo,
(viii) cyano,
(ix) phenyl,
(x) trifluoromethyl,
(xi) —$(CH_2)_m$—$NR^9R^{10}$ wherein m is 0, 1 or 2, and $R^9$ and $R^{10}$ are as defined above,
(xii) —$NR^9COR^{10}$, wherein $R^9$ and $R^{10}$ are as defined above,
(xiii) —$CONR^9R^{10}$, wherein $R^9$ and $R^{10}$ are as defined above,
(xiv) —$CO_2R^9$, wherein $R^9$ is as defined above, and
(xv) —$(CH_2)_m$—$OR^9$, wherein m and $R^9$ are as defined above;

p is 0 or 1;
X is selected from:
(a) —$PO(OH)O^{31} \cdot M^+$, wherein $M^+$ is a pharmaceutically acceptable monovalent counterion,
(b) —$PO(O^-)_2 \cdot 2M^+$,
(c) —$PO(O^-)_2 D^{2+}$, wherein $D^{2+}$ is a pharmaceutically acceptable divalent counterion,
(d) —$CH(R^4)$—$PO(OH)O^- \cdot M^+$, wherein $R^4$ is hydrogen or $C_{1-3}$alkyl,
(e) —$CH(R^4)$—$PO(O^-)_2 \cdot 2M^+$,
(f) —$CH(R^4)$—$PO(O^-)_2 \cdot D^{2+}$,
(g) —$SO_3^- \cdot M^+$,
(h) —$CH(R^4)$—$SO_3^- \cdot M^+$,
(i) —$CO$—$CH_2CH_2$—$CO_2^- \cdot M^+$,
(j) —$CH(CH_3)$—$O$—$CO$—$R^5$, wherein $R^5$ is selected from the group consisting of:

(i)

(ii)
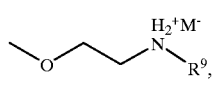

(iii)
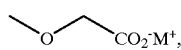

(iv)
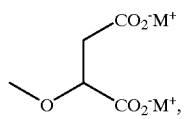

(v)
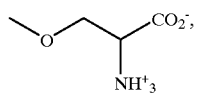

(vi)
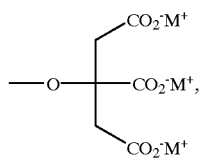

(vii)
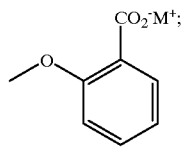

and
(k) hydrogen, with the proviso that if p is 0 and none of $R^{11}$, $R^{12}$ or $R^{13}$ are —OX, then X is other than hydrogen;

Y is selected from the group consisting of:
(1) a single bond,
(2) —O—,
(3) —S—,
(4) —CO—,
(5) —$CH_2$—,
(6) —$CHR^{1b}$—, and
(7) —$CR^{15}R^{16}$—, wherein $R^{15}$ and $R^{16}$ are independently selected from the group consisting of:
(a) $C_{1-6}$alkyl, unsubstituted or substituted with one or more of the substituents selected from:

(i) hydroxy,
(ii) oxo,
(iii) $C_{1-6}$alkoxy,
(iv) phenyl-$C_{1-3}$alkoxy,
(v) phenyl,
(vi) —CN,
(vii) halo,
(viii) —NR$^9$R$^{10}$, wherein R$^9$ and R$^{10}$ are as defined above,
(ix) —NR$^9$COR$^{10}$, wherein R$^9$ and R$^{10}$ are as defined above,
(x) —NR$^9$CO$_2$R$^{10}$, wherein R$^9$ and R$^{10}$ are as defined above,
(xi) —CONR$^9$R$^{10}$, wherein R$^9$ and R$^{10}$ are as defined above,
(xii) —COR$^9$, wherein R$^9$ is as defined above, and
(xiii) —CO$_2$R$^9$, wherein R$^9$ is as defined above;
(b) phenyl, unsubstituted or substituted with one or more of the substituent(s) selected from:
(i) hydroxy,
(ii) $C_{1-6}$alkoxy,
(iii) $C_{1-6}$alkyl,
(iv) $C_{2-5}$alkenyl,
(v) halo,
(vi) —CN,
(vii) —NO$_2$,
(viii) —CF$_3$,
(ix) —(CH$_2$)$_m$—NR$^9$R$^{10}$, wherein m, R$^9$ and R$^{10}$ are as defined above,
(x) —NR$^9$COR$^{10}$, wherein R$^9$ and R$^{10}$ are as defined above,
(xi) —NR$^9$CO$_2$R$^{10}$, wherein R$^9$ and R$^{10}$ are as defined above,
(xii) —CONR$^9$R$^{10}$, wherein R$^9$ and R$^{10}$ are as defined above,
(xiii) —CO$_2$NR$^9$R$^{10}$, wherein R$^9$ and R$^{10}$ are as defined above,
(xiv) —COR$^9$, wherein R$^9$ is as defined above, and
(xv) —CO$_2$R$^9$, wherein R$^9$ is as defined above;
Z is selected from:
(1) hydrogen,
(2) $C_{1-6}$alkyl, and
(3) hydroxy, with the proviso that if Y is —O—, Z is other than hydroxy, or if Y is —CHR$^{15}$—, then Z and R$^{15}$ may be joined together to form a double bond.

Particularly preferred compounds of formula (III) are those wherein:
R$^2$ and R$^3$ are independently selected from the group consisting of:
(1) hydrogen,
(2) $C_{1-6}$alkyl,
(3) $C_{1-6}$alkenyl, and
(4) phenyl;
R$^6$, R$^7$ and R$^8$ are independently selected from the group consisting of:
(1) hydrogen,
(2) $C_{1-6}$alkyl,
(3) fluoro,
(4) chloro,
(5) bromo,
(6) iodo, and
(7) —CF$_3$;
R$^{11}$, R$^{12}$ and R$^{13}$ are independently selected from the group consisting of:
(1) fluoro,
(2) chloro,
(3) bromo, and
(4) iodo;
A is unsubstituted $_{1-6}$alkyl;
B is selected from the group consisting of:

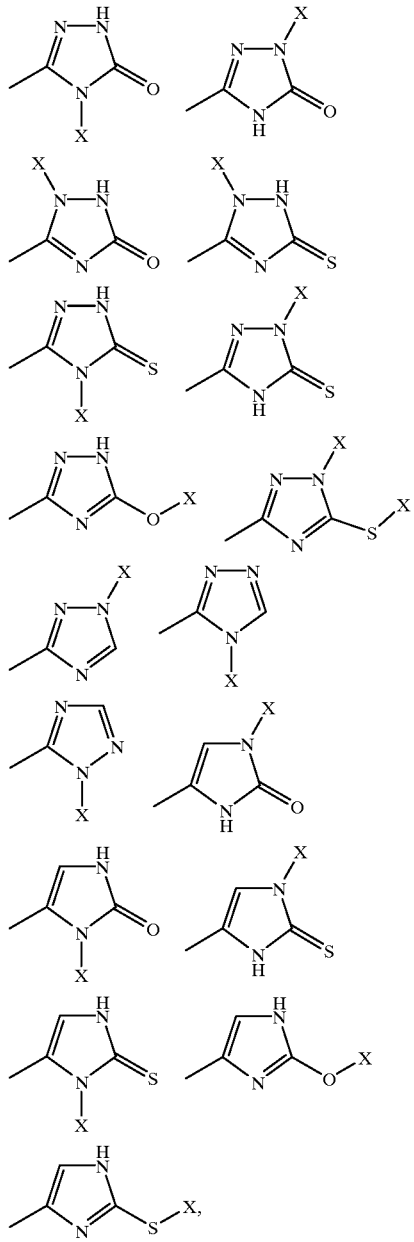

p is 0 or 1;
X is selected from:
(a) —PO(OH)O$^-$•M$^+$, wherein M$^+$ is a pharmaceutically acceptable monovalent counterion,
(b) —PO(O$^-$)$_2$•2M$^+$,
(c) —PO(O$^-$)$_2$•D$^{2+}$, wherein D$^{2+}$ is a pharmaceutically acceptable divalent counterion,
(d) —CH(R$^4$)—PO(OH)O$^-$•M$^+$, wherein R$^4$ is hydrogen or $C_{1-3}$alkyl,
(e) —CH(R$^4$)—PO(O$^-$)$_2$•2M$^+$,
(f) —CH(R$^4$)—PO(O$^-$)$_2$•D$^{2+}$,
(i) —CO—CH$_2$CH$_2$—CO$_2$$^-$•M$^+$, (j) —CH(CH₃)—O—CO—R⁵, wherein R⁵ is selected from the group consisting of:

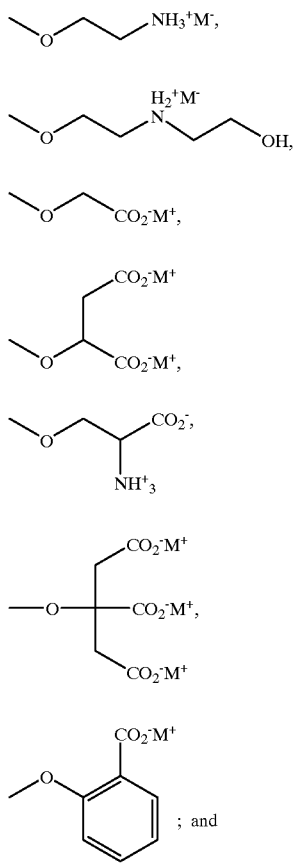

Y is —O—;
Z is hydrogen or $C_{1-6}$alkyl;
and pharmaceutically acceptable salts thereof.

Particularly preferred compounds of formula (III) include:

(1) 2-(S)-(3,5-bis(trifluoromethyl)benzyloxy)-3-(S)-phenyl-4-(3-(5-oxo-1H,4H-1,2,4-triazolo)methyl)morpholine N-oxide;

(2) 2-(S)-(3,5-bis(trifluoromethyl)benzyloxy)-3-(S)-phenyl-4-(3-(4-(ethoxycarbonyloxy-1-ethyl)-5-oxo-1H-1,2,4-triazolo)methyl)morpholine;

(3) 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine;

(4) 2-(R)-(1-(R)-(3,5-bis(trifluoromethyl)phenyl)ethoxy)-3-(S)-(4-fluorophenyl)-4-(3-(1-monophosphoryl-5-oxo-1H-1,2,4-triazolo)methyl)morpholine;

(5) 2-(R)-(1-(R)-(3,5-bis(trifluoromethyl)phenyl)ethoxy)-3-(S)-(4-fluorophenyl)-4-(3-(2-monophosphoryl-5-oxo-1H-1,2,4-triazolo)methyl)morpholine;

(6) 2-(R)-(1-(R)-(3,5-bis(trifluoromethyl)phenyl)ethoxy)-3-(S)-(4-fluorophenyl)-4-(3-(5-oxyphosphoryl-1H-1,2,4-triazolo)methyl)morpholine;

(7) 2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

and pharmaceutically acceptable salts thereof

Further preferred CNS-penetrant NK-1 receptor antagonists are those described in European Patent Specification No. WO 96/05181, i.e. compounds of formula (IV):

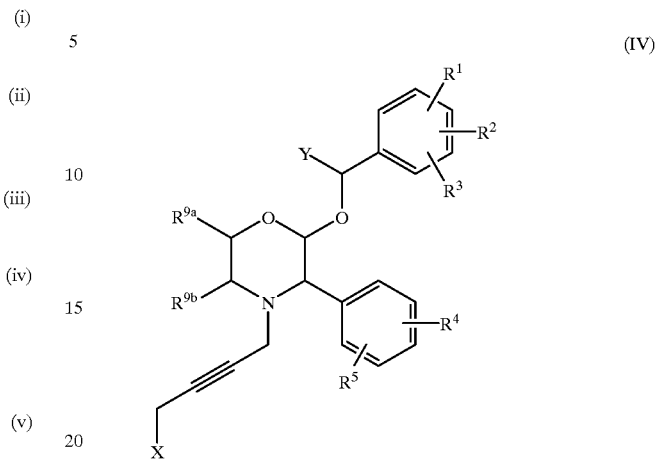

wherein

X is a group of the formula $NR^6R^7$ or a C- or N-linked imidazolyl ring;

Y is hydrogen or $C_{1-4}$alkyl optionally substituted by a hydroxy group;

$R^1$ is hydrogen, halogen, $C_{1-6}$alkyl, $C_{1-6}$alkoxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ each independently represent hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, hydroxy, $CF_3$, $NO_2$, CN, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

$R^5$ is hydrogen, halogen, $C_{1-6}$alkyl, $C_{1-6}$alkoxy substituted by $C_{1-4}$alkoxy or $CF_3$;

$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

$R^7$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, $S(O)$ or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $CO_2R^a$ where $R^a$ is as previously defined;

or $R^6$ and $R^7$ together with the nitrogen atom to which they are attached, form a non-aromatic azabicyclic ring system of 6 to 12 ring atoms;

$R^8$ is hydrogen, $C_{1-4}$alkyl, hydroxy$C_{1-4}$alkyl or $C_{1-4}$alkoxy$C_{1-4}$alkyl; and $R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

and pharmaceutically acceptable salts thereof.

Particularly preferred compounds of formula (IV) are those of formula (IVa) and pharmaceutically acceptable salts thereof:

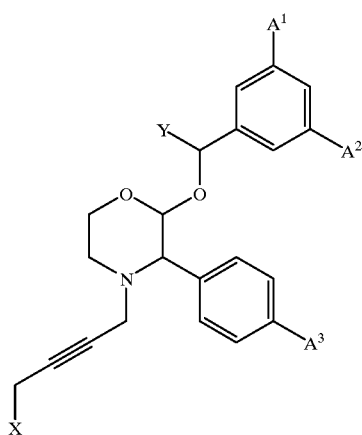

(IVa)

wherein
$A^1$ is fluorine or $CF_3$;
$A^2$ is fluorine or $CF_3$;
$A^3$ is fluorine or hydrogen;
and X and Y are as defined in relation to formula (I).

Specific compounds of formula (IV) of use in the present invention include:

2-(R)-(1-(R)-(3,5-bis(trifluoromethyl)p-henyl)ethoxy)-3-(S)-(4-fluorophenyl)-4-(4-morpholinobut-2-yn-yl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine;

4-(4-azetidinylbut-2-yn-yl)-2-(R)-(1-(R)-(3,5-bis(trifluoromethyl)phenyl) ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-imidazolylbut-2-yn-yl)morpholine;

2-(R)-(1-(R)-(3,5-bis(trifluoromethyl)phenyl)ethoxy)-3-(S)-(4-fluorophenyl)-4-(4-(N-methylpiperazinyl)but-2-yn-yl)morpholine;

4-(4-bis(2-methoxyethyl)aminobut-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-pyrrolidinobut-2-yn-yl)morpholine;

3-(S)-(4-fluorophenyl)-2-(R)-(1-(R)-(3-fluoro-5-(trifluoromethyl)phenyl) ethoxy)-4-(4-morpholinobut-2-yn-yl)morpholine;

3-(S)-(4-fluorophenyl)-4-(4-morpholinobut-2-yn-yl)-2-(R)-(1-(R)-(3-(trifluoromethyl)phenyl)ethoxy)morpholine;

4-(4-azetidinylbut-2-yn-yl)-3-(S)-(4-fluorophenyl)-2-(R)-(1-(R)-(3-(trifluoromethyl)phenyl)ethoxy)morpholine;

2-(R)-(1-(R)-(3,5-bis(trifluoromethyl)phenyl)ethoxy)-4-(4-(N-(2-methoxyethyl)-N-methyl)aminobut-2-yn-yl)-3-(S)-phenylmorpholine;

2-(R)-(1-(R)-(3,5-bis(trifluoromethyl)phenyl)ethoxy)-4-(4-(N-cyclopropyl-N-(2-methoxyethyl)amino)but-2-yn-yl)-3-(S)-phenylmorpholine;

2-(R)-(1-(R)-(3,5-bis(trifluoromethyl)phenyl)ethoxy)-4-(4-(N-isopropyl-N-(2-methoxyethyl)amino)but-2-yn-yl)-3-(S)-phenylmorpholine;

4-(4-(N,N-dimethylamino)but-2-yn-yl)-3-(S)-(4-fluorophenyl)-2-(R)-(1-(S)-(3-fluoro-5-(trifluoromethyl)phenyl-2-hydroxyethoxy)morpholine;

4-(4-azetidinylbut-2yn-yl)-3-(S)-(4-fluorophenyl)-2-(R)-(1-(S)-(3-fluoro-5-(trifluoromethyl)phenyl)-2-hydroxyethoxy)morpholine;

2-(R)-(1-(S)-(3,5-bis(trifluoromethyl)phenyl)-2-hydroxyethoxy)-4-(4-(N,N-dimethylamino)but-2-yn-yl)-3-(S)-(4-fluorophenyl)morpholine;

4-(4-azetidinylbut-2-yn-yl)-2-(R)-(1-(S)-(3,5-bis(trifluoromethyl)phenyl-2-hydroxyethoxy)-3-(S)-(4-fluorophenyl)morpholine;

4-(4-N-bis(2-methoxy)ethyl-N-methylamino)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(4-(2-(S)-(methoxymethyl)pyrrolidino)but-2-yn-yl)morpholine;

4-(4-(7-azabicyclo[2.2.1]heptano)but-2-yn-yl)-2-(R)-(1-(R)-(3,5-bis(trifluoromethyl)phenyl)ethoxy)-3-(S)-(4-fluorophenyl)morpholine;

2-(R)-(1-(R)-(3,5-bis (trifluoromethyl)phenyl)ethoxy)-4-(4-diisopropylaminobut-2-yn-yl)-3-(S)-(4-fluorophenyl)morpholine;

2-(R)-(1-(R)-(3-fluoro-5-(trifluoromethyl)phenyl)ethoxy)-4-(4-( 2-(S)-(methoxymethyl)pyrrolidino)but-2-yn-yl)-3-(S)-phenylmorpholine;

2-(R)-(1-(R)-(3,5-bis(trifluoromethyl)phenyl)ethoxy)-3-(S)-(4-fluorophenyl)-4-(4-(2-(S)-(hydroxymethyl)pyrrolidino)but-2-yn-yl)morpholine;

and pharmaceutically acceptable salts thereof.

Further preferred CNS-penetrant NK-1 receptor antagonists are those described in European Patent Specification No. WO 96/07649, i.e. compounds of formula (V):

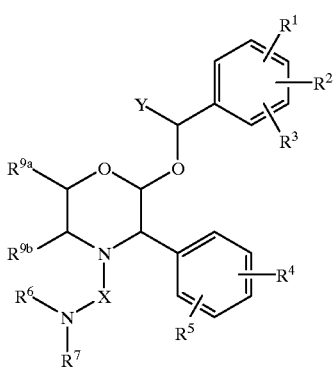

(V)

wherein

R¹ is hydrogen, halogen, $C_{1-6}$alkyl, $C_{1-6}$alkoxy, $CF_3$, $NO_2$, CN, $CO_2R^a$, $CONR^aR^b$, $C_{2-6}$alkenyl, $C_{2-6}$alkynyl or $C_{1-4}$alkyl substituted by $C_{1-4}$alkoxy, and wherein $R^a$ and $R^b$ are each independently hydrogen or $C_{1-4}$alkyl;

R² is hydrogen, halogen, $C_{1-6}$alkyl, $C_{1-6}$alkoxy substituted by $C_{1-4}$alkoxy or $CF_3$;

R³ is hydrogen, halogen or $CF_3$;

R⁴ is hydrogen, halogen, $C_{1-6}$alkyl, $C_{1-6}$alkoxy, hydroxy, $CF_3$, $NO_2$, CN, $CO_2R^a$, $CONR^aR^b$, $C_{2-6}$alkenyl, $C_{2-6}$alkynyl or $C_{1-4}$alkyl substituted by $C_{1-4}$alkoxy, wherein $R^a$ and $R^b$ are as previously defined;

R⁵ is hydrogen, halogen, $C_{1-6}$alkyl, $C_{1-6}$alkoxy substituted by $C_{1-4}$alkoxy or $CF_3$;

R⁶ is hydrogen, $C_{1-6}$alkyl, $C_{3-7}$cycloalkyl, $C_{3-7}$cycloalkyl$_{1-4}$alkyl, phenyl, or $C_{2-4}$alkyl substituted by $C_{1-4}$alkoxy or hydroxy;

R⁷ is hydrogen, $C_{1-6}$alkyl, $C_{3-7}$cycloalkyl, $C_{3-7}$cycloalkyl$C_{1-4}$alkyl, phenyl, $C_{2-4}$alkyl substituted by $C_{1-4}$alkoxy or hydroxy, or the group C(=NR^c)NR^aR^b, where $R^a$ and $R^b$ are as previously defined and $R^c$ is hydrogen, $C_{1-6}$alkyl, CN or $COR^a$;

or R⁶ and R⁷, together with the nitrogen atom to which they are attached, form a saturated heterocyclic ring of 4 to 7 ring atoms which may optionally contain in the ring one oxygen or sulphur atom or a group selected from $NR^8$, S(O) or $S(O)_2$ and which ring may be optionally substituted by one or two groups selected from phenyl, benzyl, hydroxy$C_{1-4}$alkyl, $C_{1-4}$alkoxy$C_{1-4}$alkyl, hydroxy, oxo, $COR^a$ or $CO_2R^a$ where $R^a$ is as previously defined;

or R⁶ and R⁷, together with the nitrogen atom to which they are attached, form a piperidino ring substituted by a spiro-fused indene or indoline group, each of which may be unsubstituted or substituted on any available carbon atom by a group selected from $C_{1-6}$alkyl, $C_{1-6}$alkoxy, hydroxy, halogen, cyano, trifluoromethyl, $SO_2C_{1-6}$alkyl, $NR^aR^b$, $NR^aCOR^b$ or $CONR^aR^b$; or, in the case of an indoline group, on the nitrogen atom by a group selected from $C_{1-6}$alkyl, $C_{3-7}$cycloalkyl, $C_{3-7}$cycloalkyl$C_{1-4}$alkyl, phenyl$C_{1-4}$alkyl, $CO_2R^a$, $CONR^aR^b$, $SOR^a$ or $SO_2R^a$, where $R^a$ and $R^b$ are as previously defined;

R⁸ is hydrogen, $C_{1-4}$alkyl, hydroxy$C_{1-4}$alkyl or $C_{1-4}$alkoxy$C_{1-4}$alkyl;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is selected from $-CH_2CH_2-$, $-COCH_2-$ or $-CH_2CO-$; and

Y is hydrogen, or $C_{1-4}$alkyl optionally substituted by a hydroxyl group;

or a pharmaceutically acceptable salt thereof

Particularly preferred compounds of formula (V) are those of formula (Va) and pharmaceutically acceptable salts thereof:

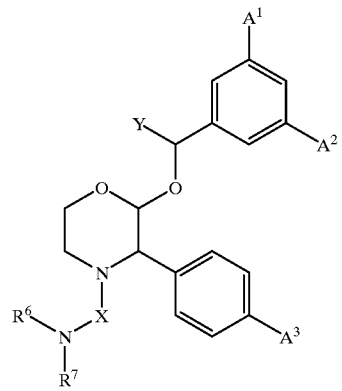

(Va)

wherein

A¹ is hydrogen, fluorine or $CF_3$;

A² is fluorine or $CF_3$;

A³ is fluorine or hydrogen;

and X, Y, R⁶ and R⁷ are as defined in relation to formula (V).

Specific compounds of formula (V) of use in the present invention include:

4-(2-aminoethyl)-2-(R)-(1-(R)-(3,5-bis(trifluoromethyl)phenyl)ethoxy)-3-(S)-(4-fluorophenyl)morpholine;

2-(R)-(1-(R)-(3,5-bis(trifluoromethyl)phenyl)ethoxy)-3-(S)-(4-fluorophenyl)-4-(2-pyrrolidinoethyl)morpholine;

2-(R)-(1-(R)-(3,5-bis(trifluoromethyl)phenyl)ethoxy)-3-(S)-(4-fluorophenyl)-4-(2-morpholinoethyl)morpholine;

2-(R)-(1-(R)-(3,5-bis(trifluoromethyl)phenyl)ethoxy)-4-(2-( 2'-(S)-carboxypyrrolidino)ethyl)-3-(S)-(4-fluorophenyl)morpholine;

2-(R)-(1-(R)-(3,5-bis(trifluoromethyl)phenyl)ethoxy)-3-(S)-(4-fluorophenyl)-4-(2-(2'-(R)-hydroxymethylpyrrolidino)ethyl)morpholine;

2-(R)-(1-(R)-(3,5-bis(trifluoromethyl)phenyl)ethoxy)-4-(2-(4'-carbomethoxy-2'-oxopyrrolidino)ethyl)-3-(S)-(4-fluorophenyl)morpholine;

2-(R)-(1-(R)-(3,5-bis(trifluoromethyl)phenyl)ethoxy)-4-(2-(N'-carboethoxy)-guanidino)ethyl)-3-(S)-(4-fluorophenyl)morpholine;

2-(R)-(1-(R)-(3,5-bis(trifluoromethyl)phenyl)ethoxy)-3-(S)-phenyl-4-(2-(4-phenylpiperidino)ethyl)morpholine;

3-(S)-phenyl-4-(2-(4-phenylpiperidino)ethyl)-2-(R)-(1-(R)-(3-(trifluoromethyl)phenyl)ethoxy)morpholine;

2-(R)-(1-(R)-(3-fluoro-5-(trifluoromethyl)phenyl)ethoxy)-3-(S)-phenyl-4-(2-(spiro(indene-3',4-piperidino))ethyl)morpholine;

2-(R)-(1-(R)-(3-fluoro-5-(trifluoromethyl)phenyl)ethoxy)-3-(S)-phenyl-4-(2-(4-phenylpiperidino)ethyl)morpholine;

2-(R)-(1-(R)-(3-fluoro-5-(trifluoromethyl)phenyl)ethoxy)-4-(2-(1'-methylsulfonyl-spiro(indoline-3',4-piperidino))ethyl)-3-(S)-phenylmorpholine;

2-(R)-(1-(R)-(3-fluoro-5-(trifluoromethyl)phenyl)ethoxy)-3-(S)-p henyl-4-(2-(4-piperidino)ethyl)morpholine;

2-(S)-(3,5-bis(trifluoromethyl)phenyl)methyloxy)-3-(S)-phenyl-4-(2-(4-phenylpiperidino)ethyl)morpholine;

4-(2-(4-benzylpiperidino)ethyl)-2-(S)-(3,5-bis (trifluoromethyl)phenyl)-methyloxy)-3-(S)-phenylmorpholine;

and pharmaceutically acceptable salts thereof.

The preferred compounds of formulae (I), (II), (III), (IV) and (V) will have the 2- and 3-substituents on the morpholine ring in the cis arrangement, the preferred stereochemistry being as shown in the following general formula:

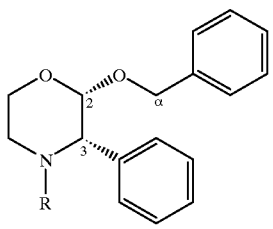

Where the benzyloxy moiety is α-substituted, the preferred stereochemistry of the α-carbon is either (R) when the substituent is an alkyl (e.g. methyl) group or (S) when the substituent is a hydroxyalkyl (e.g. hydroxymethyl) group.

Unless otherwise defined herein, suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tert-butyl.

Unless otherwise defined herein, suitable alkenyl groups include straight-chained and branched alkenyl groups containing from 2 to 6 carbon atoms. Typical examples include vinyl and allyl groups.

Unless otherwise defined herein, suitable alkynyl groups include straight-chained and branched alkynyl groups containing from 2 to 6 carbon atoms. Typical examples include ethynyl and propargyl groups.

Unless otherwise defined herein, suitable cycloalkyl groups include groups containing from 3 to 7 carbon atoms. Particular cycloalkyl groups are cyclopropyl and cyclohexyl.

Unless otherwise defined herein, suitable aryl groups include phenyl and naphthyl groups.

A particular aryl-$C_{1-6}$alkyl, e.g. phenyl-$C_{1-6}$alkyl, group is benzyl.

Unless otherwise defined herein, suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups.

The term "halogen" as used herein includes fluorine, chlorine, bromine and iodine.

The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the CNS-penetrant NK-1 receptor antagonists of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulphuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Suitable pharmaceutically acceptable salts of the antidepressant or anti-anxiety agent of use in the present invention include those salts described above in relation to the salts of CNS-penetrant NK-1 receptor antagonists.

The present invention accordingly provides the use of a CNS-penetrant NK-1 receptor antagonist selected from the compounds of formulae (I), (II), (III), (IV) and (V) and an antidepressant or anti-anxiety agent for the manufacture of a medicament for the treatment or prevention of depression and/or anxiety.

The present invention also provides a method for the treatment or prevention of depression and/or anxiety, which method comprises administration to a patient in need of such treatment an amount of a CNS-penetrant NK-1 receptor antagonist selected from the compounds of formulae (I), (II), (III), (IV) and (V) and an amount of an antidepressant or anti-anxiety agent such that together they give effective relief In a further aspect of the present invention, there is provided a pharmaceutical composition comprising a CNS-penetrant NK-1 receptor antagonist selected from the compounds of formulae (I), (II), (III), (IV) and (V) and an antidepressant or anti-anxiety agent together with at least one pharmaceutically acceptable carrier or excipient.

It will be appreciated that the CNS-penetrant NK-1 receptor antagonist selected from the compounds of formulae (I), (II), (III), (IV) and (V) and and an antidepressant or anti-anxiety agent may be present as a combined preparation for simultaneous, separate or sequential use for the treatment or prevention of depression and/or anxiety. Such combined preparations may be, for example, in the form of a twin pack.

In a further or alternative aspect of the present invention, there is therefore provided a product comprising a CNS-penetrant NK-1 receptor antagonist selected from the compounds of formulae (I), (II), (III), (IV) and (V) and and an antidepressant or anti-anxiety agent as a combined preparation for simultaneous, separate or sequential use in the treatment or prevention of depression and/or anxiety.

In a preferred aspect, the present invention accordingly provides the use of a CNS-penetrant NK-1 receptor antagonist selected from the compounds of formulae (I), (II), (III), (IV) and (V) and an antidepressant agent selected from the group consisting of: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, a-adrenoreceptor antagonists and atypical antidepressants, for the manufacture of a medicament for the treatment or prevention of depression and/or anxiety.

The present invention also provides a method for the treatment or prevention of depression and/or anxiety, which method comprises administration to a patient in need of such treatment an amount of a CNS-penetrant NK-1 receptor antagonist selected from the compounds of formulae (I), (II), (III), (IV) and (V) and an antidepressant agent selected from the group consisting of: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, α-adrenoreceptor antagonists and atypical antidepressants, such that together they give effective relief.

In a further aspect of the present invention, there is provided a pharmaceutical composition comprising a CNS-penetrant NK-1 receptor antagonist selected from the compounds of formulae (I), (II), (III), (IV) and (V) and an antidepressant agent selected from the group consisting of: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, α-adrenoreceptor antagonists and atypical antidepressants, together with at least one pharmaceutically acceptable carrier or excipient.

In a further or alternative aspect of the present invention, there is provided a product comprising a CNS-penetrant NK-1 receptor antagonist selected from the compounds of formulae (I), (II), (III), (IV) and (V) and an antidepressant agent selected from the group consisting of: norepinephrine reuptake inhibitors, selective serotonin reuptake inhibitors, monoamine oxidase inhibitors, reversible monoamine oxidase inhibitors, serotonin and noradrenaline reuptake inhibitors, corticotropin releasing factor (CRF) antagonists, α-adrenoreceptor antagonists and atypical antidepressants, as a combined preparation for simultaneous, separate or sequential use in the treatment or prevention of depression and/or anxiety.

A particularly preferred class of antidepressant agent is the selective serotonin reuptake inhibitors, thus in a further preferred aspect, the present invention accordingly provides the use of a CNS-penetrant NK-1 receptor antagonist selected from the compounds of formulae (I), (II), (III), (IV) and (V) and a selective serotonin reuptake inhibitor for the manufacture of a medicament for the treatment or prevention of depression and/or anxiety.

The present invention also provides a method for the treatment or prevention of depression and/or anxiety, which method comprises administration to a patient in need of such treatment an amount of a CNS-penetrant NK-1 receptor antagonist selected from the compounds of formulae (I), (II), (III), (IV) and (V) and an amount of a selective serotonin reuptake inhibitor, such that together they give effective relief.

In a further aspect of the present invention, there is provided a pharmaceutical composition comprising a CNS-penetrant NK-1 receptor antagonist selected from the compounds of formulae (I), (II), (III), (IV) and (V) and a selective serotonin reuptake inhibitor, together with at least one pharmaceutically acceptable carrier or excipient.

In a further or alternative aspect of the present invention, there is provided a product comprising a CNS-penetrant NK-1 receptor antagonist selected from the compounds of formulae (I), (II), (III), (IV) and (V) and a selective serotonin reuptake inhibitor as a combined preparation for simultaneous, separate or sequential use in the treatment or prevention of depression and/or anxiety.

A particularly preferred class of anti-anxiety agent is the 5-HT$_{1A}$ agonists or antagonists, especially the 5-HT$_{1A}$ partial agonists, thus in a further preferred aspect, the present invention accordingly provides the use of a CNS-penetrant NK-1 receptor antagonist selected from the compounds of formulae (I), (II), (III), (IV) and (V) and a 5-HT$_{1A}$ receptor agonist or antagonist for the manufacture of a medicament for the treatment or prevention of depression and/or anxiety.

The present invention also provides a method for the treatment or prevention of depression and/or anxiety, which method comprises administration to a patient in need of such treatment an amount of a CNS-penetrant NK-1 receptor antagonist selected from the compounds of formulae (I), (II), (III), (IV) and (V) and an amount of a 5-HT$_{1A}$ receptor agonist or antagonist, such that together they give effective relief.

In a further aspect of the present invention, there is provided a pharmaceutical composition comprising a CNS-penetrant NK-1 receptor antagonist selected from the compounds of formulae (I), (II), (III), (IV) and (V) and a 5-HT$_{1A}$ receptor agonist or antagonist, together with at least one pharmaceutically acceptable carrier or excipient.

In a further or alternative aspect of the present invention, there is provided a product comprising a CNS-penetrant NK-1 receptor antagonist selected from the compounds of formulae (I), (II), (III), (IV) and (V) and a 5-HT$_{1A}$ receptor agonist or antagonist as a combined preparation for simultaneous, separate or sequential use in the treatment or prevention of depression and/or anxiety.

As stated above, the CNS-penetrant NK-1 receptor antagonist and the antidepressant or anti-anxiety agent may be formulated in a single pharmaceutical composition or alternatively in individual pharmaceutical compositions for simultaneous, separate or sequential use in accordance with the present invention.

It will be appreciated that it may be desirable to combine the CNS-penetrant NK-1 receptor antagonist with more than one antidepressant and/or anti-antiety agent. Thus "triple combination" or "multiple combination" therapy is envisaged within the scope of the present invention, for example, use of a CNS-penetrant NK-1 receptor antagonist of formulae (I), (II), (III), (IV) or (V) in combination with a selective serotonin reuptake inhibitor, such as fluoxetine, and a compound with 5-HT$_{1A}$ antagonist activity, such as pindolol.

Preferably the compositions according to the present invention are in unit dosage forms such as tablets, pills, capsules, wafers and the like. Additionally, the active ingredients may be presented as granules or powders for extemporaneous formulation as volume defined solutions or suspensions. Alternatively, the active ingredients may be presented in ready-prepared volume defined solutions or suspensions. Preferred forms are tablets and capsules.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions of the present invention may also be administered via the buccal cavity using conventional technology, for example, absorption wafers.

Compositions in the form of tablets, pills, capsules or wafers for oral administration are particularly preferred.

The present invention further provides a process for the preparation of a pharmaceutical composition comprising a CNS-penetrant NK-1 receptor antagonist and an antidepressant or anti-anxiety agent, which process comprises bringing a CNS-penetrant NK-1 receptor antagonist and an antidepressant or anti-anxiety agent, into association with a pharmaceutically acceptable carrier or excipient.

When administered in combination, either as a single or as separate pharmaceutical composition(s), the CNS-penetrant NK-1 receptor antagonist and an antidepressant or anti-anxiety agent, are presented in a ratio which is consistent with the manifestation of the desired effect. In particular, the ratio by weight of the CNS-penetrant NK-1 receptor antagonist and the antidepressant or anti-anxiety agent will suitably be between 0.001 to 1 and 1000 to 1, and especially between 0.01 to 1 and 100 to 1.

A suitable dosage level for the CNS-penetrant NK-1 receptor antagonist about 0.05 to 1500 mg per day, preferably about 0.25 to 1500 mg per day, and especially about 0.25 to 500 mg per day. The compounds may be administered on a regimen of up to 6 times per day, preferably 1 to 4 times per day, especially 2 times per day and most especially once daily.

A suitable dosage level for the antidepressant agent is about 0.5 to 1500 mg per day, preferably about 2.5 to 1000 mg per day, and especially about 2.5 to 500 mg per day. The compounds may be administered on a regimen of up to 6 times per day, preferably 1 to 4 times per day, especially 2 times per day and most especially once daily.

A suitable dosage level for the anti-anxiety agent is about 0.5 to 1500 mg per day, preferably about 2.5 to 1000 mg per day, and especially about 2.5 to 500 mg per day. The compounds may be administered on a regimen of up to 6 times per day, preferably 1 to 4 times per day, especially 2 times per day and most especially once daily.

It will be appreciated that the amount of the CNS-penetrant NK-1 receptor antagonist and the antidepressant or anti-anxiety agent required for use in the treatment or prevention of depression and/or anxiety will vary not only with the particular compounds or compositions selected but also with the route of administration, the nature of the condition being treated, and the age and condition of the patient, and will ultimately be at the discretion of the patient's physician or pharmacist.

As used herein the term "patient" includes animals of economic importance such as bovine, ovine, and porcine animals, especially those that produce meat, as well as domestic animals (e.g. cats and dogs), sports animals (e.g. horses), zoo animals, and humans, the latter being preferred.

The compounds of formulae (I), (II), (III), (IV) and (V) may be prepared by the methods described in EP-A-0 577 394 (or WO 95/16679), WO 95/18124, WO 95/23798, WO 96/05181 and WO 96/07649, respectively.

As used herein, the term "CNS-penetrant" refers to NK-1 receptor antagonists which are able to inhibit NK-1 receptor antagonist-induced foot-tapping in the gerbil as hereinafter defined.

Essentially, hind foot-tapping in the gerbil induced by infusion of the NK-1 receptor agonist, GR73632 (d Ala[L-Pro$^9$,Me-Leu$^{10}$]-substance P-(7-11)), under anaesthesia, directly into the central ventricles is inhibited when a CNS-penetrant NK-1 receptor antagonist is administered intravenously immediately prior to GR73632 challenge, wherein hind foot-tapping over a period of five minutes following recovery from the anaesthesia is inhibited with an $ID_{50} \leq 3$ mg/kg, and preferably with an $ID_{50} \leq 1$ mg/kg.

In an alternative method, the NK-1 receptor antagonist is administered orally, 1 hour prior to GR73632 challenge, wherein the foot-tapping over a period of five minutes following recovery from anaesthesia is inhibited with an $ID_{50} \leq 30$ mg/kg, and preferably with an $ID_{50} \leq 10$ mg/kg.

CNS-penetrant NK-1 receptor antagonists of use in the present ivnention are also effective in the attenuation of separation-induced vocalisations by guinea-pig pups as hereinafter defined.

Essentially, a vocalisation response in guinea-pig pups is induced by isolation from their mothers and littermates, which response is attenuated when a CNS-penetrant NK-1 receptor antagonist is administered subcutaneously 30 minutes prior to isolation, wherein vocalisations during the first 15 minutes of isolation are attenuated with an $ID_{50} \leq 20$ mg/kg, preferably with an $ID_{50} \leq 10$ mg/kg, and especially with an $ID_{50} \leq 5$ mg/kg.

In an alternative method, the NK-1 receptor antagonist is administered orally, 4 hours prior to isolation, wherein vocalisations during the first 15 minutes of isolation are attenuated with an $ID_{50} \leq 20$ mg/kg, preferably with an $ID_{50} \leq 10$ mg/kg, and especially with an $ID_{50} \leq 5$ mg/kg.

Whilst it is recognised in many of the aforementioned patent specifications that NK-1 receptor antagonists may be used to treat depression and/or anxiety, there remains a need for simple and reliable methods for the identification of compounds with NK-1 receptor antagonist activity which would be effective in the treatment of depression and/or anxiety.

The present invention accordingly provides a preclinical screen for antidepressant and/or anxiolytic activity of CNS-penetrant NK-1 receptor antagonists, which comprises:

a) to a guinea-pig pup, administration of a NK-1 receptor antagonist or vehicle by intravenous, subcutaneous, intraperitoneal or oral routes;

b1) 30–60 minutes after intravenous, subcutaneous or intraperitoneal administration, socially isolating the treated guinea-pig pups by removal from their mother and littermates; or b2) up to 4 hours after oral administration, socially isolating the treated guinea-pig pups by removal from their mother and littermates;

c) recording the number or duration of vocalisations (isolation calls) during a specified period and comparing the effects on guinea-pig pups treated with NK-1 receptor antagonists against their own baseline or against guinea-pig pups that receive no test compound or vehicle.

Preferably the NK-1 receptor antagonist is administered by subcutaneous injection or orally by gavage.

An advantage of the present invention is that the guinea-pig is a mammal with human-like NK-1 receptor pharmacology.

The guinea-pig preclinical screen described herein has been shown to be sensitive not only to the anxiolytic and antidepressant effects of NK-1 receptor antagonists, but also to the effects of established anxiolytic and antidepressant drugs. Thus, for example, buspirone, diazepam, fluoxetine, and imipramine were all active in this assay ($ID_{50}$=0.5 mg/kg s.c., 0.7 mg/kg s.c., 2.7 mg/kg i.p. and 5.4 mg/kg s.c., respectively).

According to a futher aspect of the present invention, there is provided a preclinical screen for antidepressant and/or anxiolytic activity of CNS-penetrant NK-1 receptor antagonists, which comprises:

a) to a gerbil, administration of a NK-1 receptor antagonist or vehicle by intravenous, subcutaneous, intraperitoneal or oral routes;

b) administration by injection under anaesthetic of NK-1 receptor agonists or anxiogenic agents, administered centrally or systemically; or subjecting the gerbil to stressors such as single housing or foot shock;

c) recording the duration of repetitive hindfoot tapping and comparing the effects on gerbils treated with NK-1 receptor antagonists against gerbils that receive no test compound or vehicle.

Preferably the NK-1 receptor antagonist is administered by intravenous injection or orally by gavage.

Suitable NK-1 receptor agonists which elicit repetitive hindfoot tapping include GR73632 (d-Ala[L-Pro$^9$, Me-Leu$^{10}$]substance P-(7-11)), [Sar$^9$, Met(O$_2$)$^{11}$]substance P and substance P. Suitable anxiogenic agents include pentagastrin and adrenaline.

The NK-1 receptor antagonist may be administered intravenously about 5 minutes before challenge with the NK-1 receptor agonist or anxiogenic agent or before the aversive stimulation, in order to measure the acute effect of the NK-1 receptor antagonist. If oral administration is chosen, it may be preferable to administer the NK-1 receptor antagonist at least one hour prior to central injection of the NK-1 receptor agonist or anxiogenic agent, or the aversive stimulus. In order to measure the central duration of action of a NK-1 receptor antagonist, the test compound is conveniently administered approximately 24 hours prior to central injection of the NK-1 receptor agonist or anxiogenic agent, or the aversive stimulus.

Whilst there are many different genera of gerbil, the preferred genus is the Mongolian gerbil (*Meriones unguiculatus*). An advantage of the present invention is that the gerbil is a mammal with human-like NK-1 receptor pharmacology.

The preclinical screens described herein have been shown to be sensitive not only to the anxiolytic and antidepressant effects of NK-1 receptor antagonists, but also to the effects of an established antidepressant drug, imipramine ($ID_{50}$=3.8 mg/kg s.c. following foot-tapping induced by substance P) and the anxiolytic drug, buspirone ($ID_{50}$=3.4 mg/kg s.c.).

The identification of CNS-penetrant NK$_1$ receptor antagonists of use as anxiolytic or antidepressant agents is carried out as follows:

(i) Determine affinity for human NK$_1$ receptor in radioligand binding studies (Assay 1); select compounds with $IC_{50} \leq 10$ nM, preferably $IC_{50} \leq 2$ nM, especially $IC_{50} \leq 1$ nM.

(ii) Determine activity of compounds for their ability to inhibit distress vocalisations in guinea-pig pups (Assay 2)). Select compounds with $ID_{50} \leq 20$ mg/kg, and preferably $ID_{50} \leq 10$ mg/kg, and especially $ID_{50} \leq 5$ mg/kg.

According to an alternative aspect of the present invention, the identification of NK$_1$ receptor antagonists of use as anxiolytic or antidepressant agents is carried out as follows:

(i) Determine affinity for human NK$_1$ receptor in radioligand binding studies (Assay 1); select compounds with $IC_{50} \leq 10$ nM, preferably $IC_{50} \leq 2$ nM, especially $IC_{50} \leq 1$ nM.

(ii) Determine ability of compounds to penetrate CNS by their ability to inhibit foot tapping in gerbils induced by central injection of an NK$_1$ agonist (Assay 3); select compounds that inhibit foot tapping with $ID_{50} \leq 3$ mg/kg i.v., and preferably $ID_{50} \leq 1$ mg/kg i.v. when administered immediately prior to central NK$_1$ agonist challenge, or $ID_{50} \leq 30$ mg/kg p.o., and preferably $ID_{50} \leq 10$ mg/kg p.o. 1 hour prior to challenge.

(iii) Determine central duration of action of compounds in gerbil foot tapping assay following intravenous administration 24 hours prior to central NK$_1$ agonist challenge; select compounds showing $\leq 25$-fold loss of potency compared with $ID_{50}$ determined in step (ii) above with the proviso that $ID_{50} \leq 10$ mg/kg i.v., and preferably $\leq 5$ mg/kg i.v. after 24 hour pre-treatment.

Yet further preferred compounds of use as anxiolytic or antidepressant agents may be selected, according to either of the "selection cascades" described above, from those compounds which satisfy the NK-1 receptor binding criteria of step (i) which, in addition, have $\leq 5$-fold shift in affinity when incubated in the presence of human serum albumin (HSA) to show non-specific protein binding.

It will be appreciated that, if desired, the above "selection cascades" may be combined. Thus, a further method for the identification of NK-1 receptor antagonists of use as anxiolytic or antidepressant agents involves the use of Assay 1, Assay 2 and Assay 3, incorporating the selection criteria defined herein.

Particularly active CNS-penetrant NK-1 receptor antagonists include:

2-(S)-(3,5-bis(trifluoromethyl)benzyloxy)-3(S)-(4-fluorophenyl)-4-(3-( 5-oxo-1H,4H-1,2,4-triazolo)methyl)morpholine;

2-(R)-(1-(R)-(3,5-bis(trifluoromethyl)phenyl)ethoxy)-4-(3-(5-oxo-1H,4H-1,2,4-triazolo)methyl)-3-(S)-phenyl-morpholine;

2-(S)-(3,5-bis(trifluoromethyl)benzyloxy)-4-(3-(5-oxo-1H, 4H-1,2,4-triazolo)methyl)-3-(S)-phenyl-morpholine;

2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine;

2-(R)-(1-(R)-(3,5-bis(trifluoromethyl)phenyl)ethoxy)-4-( 5-(N,N-dimethylamino)methyl-1,2,3-triazol-4-yl) methyl-3-(S)-phenylmorpholine;

2-(R)-(1-(R)-(3,5-bis(trifluoromethyl)phenyl)ethoxy)-4-(5-(N,N-dimethylamino)methyl-1,2,3-triazol-4-yl) methyl-3-(S)-(4-fluorophenyl)morpholine;

2-(S)-(1-(R)-(3,5-bis(trifluoromethyl)phenyl)ethoxy)-3-(S)-(4-fluorophenyl)-4-(3-(1-monophosphoryl-5-oxo-4H-1,2,4-triazolo)methyl)morpholine;

2-(R)-(1-(R)-(3,5-bis(trifluoromethyl)phenyl)ethoxy)-4-(4-N,N-dimethylaminobut-2-yn-yl)-3-(S)-(4-fluorophenyl)morpholine; or a pharmaceutically acceptable salt thereof.

According to a further aspect of the present invention, there is provided the use of a CNS-penetrant NK-1 receptor antagonist identified according to either of the preclinical screens defined herein for the manufacture of a medicament for the treatment or prevention of depression and/or anxiety as previously defined.

Similarly, there is also provided a method for the treatment or prevention of depression and/or anxiety as previously defined, which method comprises administration to a patient in need of such treatment an effective amount of a CNS-penetrant NK-1 receptor antagonist identified according to either of the preclinical screens defined herein.

Particularly preferred CNS-penetrant NK-1 receptor antagonists of the formulae (I), (II), (III), (IV) and (V) for use in the present invention are compounds which are potent NK-1 receptor antagonists, i.e. compounds with an NK-1 receptor affinity ($IC_{50}$) of less than 100 nM. Preferably, the NK-1 receptor antagonist has $IC_{50} \leq 10$ nM, in particular $IC_{50} \leq 2$ nM, and most especially $IC_{50} \leq 1$ nM.

NK-1 receptor binding assays are well known in the art. The following assay is one such protocol based upon the displacement of $^{125}I\text{-Tyr}^8$-substance P binding to cloned human NK-1 receptors in vitro:

ASSAY 1: NK-1 Receptor Binding Assay

NK-1 receptor binding assays are performed in intact Chinese hamster ovary (CHO) cells expressing the human NK-1 receptor using a modification of the assay conditions described by Cascieri et al, *J. Pharmacol. Exp. Ther.*, 1992, 42, 458. Typically, the receptor is expressed at a level of $3 \times 10^5$ receptors per cell. Cells are grown in monolayer culture, detached from the plate with enzyme-free dissociation solution (Speciality Media Inc.), and washed prior to use in the assay. $^{125}I\text{-Tyr}^8$-substance P (0.1 nM, 2000 Ci/mmol; New England Nuclear) is incubated in the presence or absence of test compounds (dissolved in 5 µl dimethylsulphoxide, DMSO) with $5 \times 10^4$ CHO cells. Ligand binding is performed in 0.25 ml of 50 mM Tris-HCl, pH7.5, containing 5 mM $MnCl_2$, 150 mM NaCl, 0.02% bovine serum albumin (Sigma), 50 µg/ml chymostatin (Peninsula), 0.1. nM phenylmethylsulphonyl fluoride, 2 µg/ml pepstatin, 2 µg/ml leupeptin and 2.8 µg/ml furoyl saccharine. The incubation proceeds at room temperature until equilibrium is achieved (>40 minutes) and the receptor-ligand complex is harvested by filtration over GF/C filters pre-soaked in 0.1% polyethylenimine using a Tomtek 96-well harvester. Non-specific binding is determined using excess substance P (1 µM) and represents <10% of total binding.

Pharmacological assays for the study of antidepressant or anti-anxiety activity are well known in the art. Many are based upon the ability of antidepressants to support animal behaviour in stressful situations that ordinarily lead to diminished behavioural responsiveness ("learned helplessness"), such as repeated noxious shocks, forced swimming, or separation from other animals. For example, the following assay, which involves the inhibition of separation-induced vocalisations in guinea-pig pups, may be used to evaluate the methods of the present invention in the treatment or prevention of depression and/or anxiety.

ASSAY 2: Separation-Induced Vocalisation

Male and female guinea-pigs pups are housed in family groups with their mothers and littermates throughout the study. Experiments are commenced after weaning when the pups are at least 2 weeks old. Before entering an experiment, the pups may be screened to ensure that a vigorous vocalisation response is reproducibly elicited following maternal separation. The pups are placed individually in an observation cage (approximately 55 cm×39 cm×19 cm) in a room physically isolated from the home cage for approximately 15 minutes and the duration and/or number of vocalisation during this baseline period is recorded. Those animals which vocalise for longer than 5 minutes may be employed for drug challenge studies (approximately 50% of available pups may fail to reach this criterion). On test days each pup receives an oral dose or an s.c. or i.p. injection of test compound or vehicle and is then immediately returned to the home cage with its mother and siblings, typically for at least 30 to 60 minutes (or for up to 4 hours following an oral dose, dependent upon the oral pharmacokinetics of the test compound) before social isolation for 15 minutes as described above. The duration and/or number of vocalisation on drug treatment days may be expressed as a percentage of the pre-treatment baseline value for each animal or compared with values obtained in vehicle-treated animals. The same subjects may be retested once weekly for up to 6 weeks. Between 6 and 8 animals typically receive each test compound at each dose tested.

ASSAY 3: Gerbil Foot-Tapping (CNS Penetration) Assay

CNS-penetrant NK-1 receptor antagonists for use in the present invention can be identified by their ability to inhibit foot tapping in gerbils induced by anxiogenic agents (such as pentagastrin) or central infusion of NK-1 receptor agonists such as GR73632, or caused by aversive stimulation such as foot shock or single housing, based on the method of Rupniak & Williams, *Eur. J. Pharmacol.*, 1994, 265, 179.

Male or female Mongolian gerbils (35–70 g) are anaesthetised by inhalation of an isoflurane/oxygen mixture to permit exposure of the jugular vein in order to permit administration of test compounds or vehicle in an injection volume of approximately 5 ml/kg i.v. Alternatively, test compounds may be administered orally or by subcutaneous or intraperitoneal routes. A skin incision is then made in the midline of the scalp to expose the skull. An anxiogenic agent (e.g. pentagastrin) or a selective NK-1 receptor agonist (e.g. GR73632 (d Ala[L-Pro$^9$,Me-Leu$^{10}$]-substance P-(7-11)) is infused directly into the cerebral ventricles (e.g. 3 pmol in 5 µl i.c.v., depending on test substance) by vertical insertion of a cuffed 27 gauge needle to a depth of 4.5 mm below bregma. The scalp incision is closed and the animal allowed to recover from anaesthesia in a clear perspex observation box (approximately 25 cm×20 cm×20 cm). The duration and/or intensity of hind foot tapping is then recorded continuously for approximately 5 minutes. Alternatively, the ability of test compounds to inhibit foot tapping evoked by aversive stimulation, such as foot shock or single housing, may be studied using a similar method of quantification.

It will be appreciated that CNS-penetration as defined by this assay and as used herein is a property of the NK-1 receptor antagonist and is not conferred by co-administration or co-formulation of the NK-1 receptor antagonist with a carrier or excipient designed to transiently open the blood-brain barrier.

One example of a NK-1 receptor antagonist active in the preclinical screens of the present invention is the compound 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine, the preparation of which is described in International Patent Specification No. WO 95/16679. In the aforementioned assays, this compound has the following activity:

| human NK-1 receptor binding: | $IC_{50}$ = 0.1 nM |
| --- | --- |
| guinea-pig vocalisation (4 hrs. pretreatment) | $ID_{50}$ = 0.73 mg/kg p.o. |
| gerbil foot-tapping (5 mins.): | $ID_{50}$ = 0.36 mg/kg i.v. |
| gerbil foot-tapping (24 hrs.): | $ID_{50}$ = 0.33 mg/kg i.v. |

Another example of a NK-1 receptor antagonist active in the preclinical screens of the present invention is the compound 2-(R)-(1-(R)-(3,5-bis(trifluoromethyl)phenyl)ethoxy)-4-(5-(N,N-dimethylamino)methyl-1,2,3-triazol-4-yl)methyl-3-(S)-phenylmorpholine, the preparation of which is described in International Patent Specification No. WO 95/18124. In the aforementioned assays, this compound has the following activity:

| human NK-1 receptor binding: | $IC_{50}$ = 0.25 nM |
| --- | --- |
| guinea-pig vocalisation: | $ID_{50}$ = 0.5 mg/kg s.c. |
| gerbil foot-tapping (5 mins.): | $ID_{50}$ = 0.12 mg/kg i.v. |
| gerbil foot-tapping (24 hrs.): | $ID_{50}$ = 0.17 mg/kg i.v. |

Combinations of a CNS-penetrant NK-1 receptor antagonist with the anti-anxiety and antidepressant agents, buspirone and fluoxetine, have been tested in the guinea-pig vocalisation assay (Assay 3):

Test Compound A is 2-(R)-(1-(R)-(3,5-bis(trifluoromethyl)phenyl) ethoxy)-4-(5-(dimethylamino)methyl-1,2,3-triazol-4-yl)methyl-3-(S)-phenylmorpholine.

Test Compound B is the less active enantiomer of Test Compound A—i.e. 2-(S)-(1-(R)-(3,5-bis(trifluoromethyl)phenyl)ethoxy)-4-(5-(dimethylamino)methyl-1,2,3-triazol-4-yl)methyl-3-(R)-phenylmorpholine.

Test Compounds A and B and buspirone were dissolved in 0.9% saline and administered s.c. in the flank. Due to limitations of solubility, fluoxetine was suspended in 0.5% methocel and given i.p. The injection volume was 1 ml/kg.

Results

Guinea-pig pups isolated from their mothers and littermates emitted a vigorous vocalisation response during the first 15 minutes of separation (total duration approximately 8 minutes during this period). Administration of the highly CNS penetrant NK-1 receptor antagonist Test Compound A (0.25 mg/kg s.c.), buspirone (0.25 mg/kg s.c.), or fluoxetine (2 mg/kg i.p.) alone 30 minutes previously attenuated separation-induced vocalisations by approximately 25% compared with the baseline vocalisation response determined using the same animals on the previous day. Combined administration of Test Compound A (0.25 mg/kg s.c.) with either buspirone (0.25 mg/kg s.c.) or fluoxetine (2 mg/kg i.p.) virtually abolished separation-induced vocalisations (FIGS. 1 & 2). The NK-1 receptor specificity of this effect was confirmed by the failure of the less active enantiomer, Test Compound B (0.25 mg/kg s.c.) to attenuate separation-induced vocalisations when administered alone, or to potentiate the inhibitory effect of buspirone (0.25 mg/kg s.c.; FIG. 1).

The above results provide evidence for a synergistic interaction between a centrally acting NK-1 receptor antagonist (Test Compound A) with the anti-anxiety and antidepressant drugs buspirone and fluoxetine in a distress vocalisation assay using guinea-pigs. This appears to reflect a specific NK-1 receptor mediated interaction, since co-administration of the less active enantiomer, Test Compound B, at the same dose failed to potentiate the ability of buspirone to inhibit vocalisations. The findings provide the first experimental evidence that centrally acting NK-1 receptor antagonists may augment the therapeutic response to clinically used anti-anxiety and antidepressant drugs, including agents acting as agonists or antagonists at the 5-$HT_{1A}$ receptor (such as buspirone), and selective serotonin reuptake inhibitors (such as fluoxetine).

It will be appreciated from the foregoing description that an advantage of the combinations of the present invention is the oral bioavailability of the NK-1 receptor antagonists of use in such combinations. Pharmacokinetic analysis to determine the oral bioavailability of the NK-1 receptor antagonists may be effected simply by measuring the ability of the NK-1 receptor antagonist to inhibit NK-1 receptor agonist-induced foot-tapping in the gerbil following oral administration of the NK-1 receptor antagonist. Compounds with an $ID_{50} \leq 30$ mg/kg p.o., and preferably $ID_{50} \leq 10$ mg/kg p.o., following administration 1 hour prior to central NK-1 receptor agonist challenge are considered to be orally active according to the present invention.

An alternative pharmacokinetic analysis takes advantage of the ability of CNS-penetrant NK-1 receptor antagonists to atenuate cisplatin-induced emesis. Orally active, CNS-penetrant NK-1 receptor antagonists demonstrate this activity in the following assay:

ASSAY 4: Ferret Emesis

Individually housed male ferrets (1.0–2.5 kg) are dosed orally by gavage with test compound. Ten minutes later they are fed with approximately 11 g of tinned cat food. At 60 minutes following oral dosing, cisplatin (10 mg/kg) is given i.v. via a jugular vein catheter inserted under a brief period of halothane anaesthesia. The catheter is then removed, the jugular vein ligated and the skin incision closed. The ferrets recover rapidly from the anaesthetic and are mobile within 10–20 minutes. The animals are observed continuously during recovery from the anaesthetic and for 4 hours following the cisplatin injection. The numbers of retches and vomits occurring during the 4 hours after cisplatin administration are recorded by trained observers.

Oral bioavailability of the NK-1 receptor antagonist is determined by its ability to inhibit cisplatin-induced emesis in ferrets following oral administration (Assay 4). Compounds with an $ID_{90} \leq 3$ mg/kg p.o., and preferably $ID_{90} \leq 1$ mg/kg p.o., are considered to be orally active according to the present invention. Thus, for example, the NK-1 receptor antagonist 2-(R)-(1-(R)-(3,5-bis (trifluoromethyl)phenyl) ethoxy)-3-(S)-(4-fluorophenyl)-4-(3-(5-oxo-1H,4H-1,2,4-triazolo)methyl)morpholine, mentioned above, has an $ID_{90}$ in the ferret emesis assay (Assay 4) of <3 mg/kg p.o.

The following examples illustrate pharmaceutical compositions according to the invention.

These formulations may be prepared with separate active ingredients or with a combination of active ingredients in one composition. In such combined preparations, the ratio of the CNS-penetrant NK-1 receptor antagonist and the antidepressant or anti-anxiety agent will depend upon the choice of active ingredients.

EXAMPLE 1

Tablets Containing 50–300 mg of NK-1 Antagonist and 5–10 mg of Buspirone

| | Amount mg | | | | | |
| --- | --- | --- | --- | --- | --- | --- |
| NK-1 antagonist | 50.0 | 50.0 | 100.0 | 100.0 | 300.0 | 300.0 |
| buspirone | 5.0 | 10.0 | 5.0 | 10.0 | 5.0 | 10.0 |

-continued

|  | Amount mg | | | | | |
|---|---|---|---|---|---|---|
| Microcrystalline cellulose | 80.0 | 80.0 | 80.0 | 80.0 | 80.0 | 80.0 |
| Modified food corn starch | 80.0 | 80.0 | 80.0 | 80.0 | 80.0 | 80.0 |
| Lactose | 184.5 | 179.5 | 134.5 | 129.5 | 134.5 | 129.5 |
| Magnesium Stearate | 0.5 | 0.5 | 0.5 | 0.5 | 0.5 | 0.5 |

EXAMPLE 2

Tablets Containing 50–300 mg of NK-1 Antagonist and 20 mg of Fluoxetine

|  | Amount mg | | |
|---|---|---|---|
| NK-1 antagonist | 50.0 | 100.0 | 300.0 |
| fluoxetine | 20.0 | 20.0 | 20.0 |
| Microcrystalline cellulose | 80.0 | 80.0 | 80.0 |
| Modified food corn starch | 80.0 | 80.0 | 80.0 |
| Lactose | 169.5 | 119.5 | 119.5 |
| Magnesium Stearate | 0.5 | 0.5 | 0.5 |

The active ingredients cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 50 mg, 100 mg and 300 mg of the CNS-penetrant NK-1 receptor antagonist per tablet.

We claim:

1. A method for the treatment or prevention of depression or anxiety, which method comprises oral administration to a patient in need of such treatment or prevention of an amount of a NK-1 receptor antagonist and an amount of an antidepressant or anti-anxiety agent, such that together they give effective relief, wherein said NK-1 receptor antagonist is CNS-penetrant as determined by its ability to inhibit NK-1 receptor agonist-induced foot-tapping in the gerbil, and is effective in the attenuation of separation-induced vocalisations by guinea-pig pups.

2. The method of claim 1 wherein the NK-1 receptor antagonist inhibits NK-1 receptor agonist-induced foot-tapping in the gerbil with an $ID_{50} \leq 3$ mg/kg i.v. when administered immediately prior to central NK-1 receptor agonist challenge; or an $ID_{50} \leq 30$ mg/kg p.o. when administered 1 hour prior to central NK-1 receptor agonist challenge.

3. The method of claim 1 wherein the NK-1 receptor antagonist additionally shows $\leq 25$-fold loss of potency in its inhibition of NK-1 receptor agonist-induced foot-tapping in the gerbil following intravenous administration 24 hours prior to central NK-1 receptor agonist challenge, with the proviso that the $ID_{50} \leq 10$ mg/kg i.v. after 24 hour pretreatment.

4. The method of claim 1 wherein the NK-1 receptor antagonist attenuates separation-induced vocalisations by guinea-pig pups with an $ID_{50} \leq 20$ mg/kg.

5. The method of claim 1 wherein the NK-1 receptor antagonist has an affinity for the human NK-1 receptor of $IC_{50} \leq 10$ nM.

6. The method of claim 1 wherein the NK-1 receptor antagonist is a compound of formula (I):

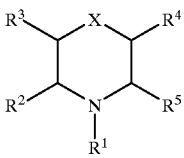

(I)

or a pharmaceutically acceptable salt thereof, wherein:

$R^1$ is selected from the group consisting of:
(1) $C_{1-6}$alkyl, substituted with one or more of the substituents selected from:
(a) heterocycle, wherein the heterocycle is selected from the group consisting of:
(A) benzimidazolyl,
(B) imidazolyl,
(C) isoxazolyl,
(D) isothiazolyl,
(E) oxadiazolyl,
(F) pyrazinyl,
(G) pyrazolyl,
(H) pyridyl,
(I) pyrrolyl,
(J) tetrazolyl,
(K) thiadiazolyl,
(L) triazolyl, and
(M) piperidinyl,
and wherein the heterocycle is unsubstituted or substituted with one or more substituent(s) selected from:
(i) $C_{1-6}$alkyl, unsubstituted or substituted with halo, —$CF_3$, —$OCH_3$, or phenyl,
(ii) $C_{1-6}$alkoxy,
(iii) oxo,
(iv) thioxo,
(v) cyano,
(vi) —$SCH_3$,
(vii) phenyl,
(viii) hydroxy,
(ix) trifluoromethyl,
(x) —$(CH_2)_m$—$NR^9R^{10}$, wherein m is 0, 1 or 2, and $R^9$ and $R^{10}$ are independently selected from:
(I) hydrogen,
(II) $C_{1-6}$alkyl,
(III) hydroxy$C_{1-6}$alkyl, and
(IV) phenyl,
(xi) —$NR^9COR^{10}$, wherein $R^9$ and $R^{10}$ are as defined above, and
(xii) —$CONR^9R^{10}$, wherein $R^9$ and $R^{10}$ are as defined above, $R^2$ and $R^3$ are independently selected from the group consisting of:
(1) hydrogen;
(2) $C_{1-6}$alkyl
(3) $C_{2-6}$alkenyl, and
(5) phenyl;

X is —O—;

$R^4$ is

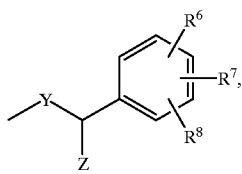

$R^5$ is phenyl, unsubstituted or substituted with halo;
$R^6$, $R^7$ and $R^8$ are independently selected from the group consisting of:
(1) hydrogen,
(2) $C_{1-6}$alkyl,
(3) halo, and
(4) —$CF_3$;
Y is —O—; and
Z is hydrogen or $C_{1-4}$alkyl.

7. The method of claim 1 wherein the NK-1 receptor antagonist is a compound of formula (IIa):

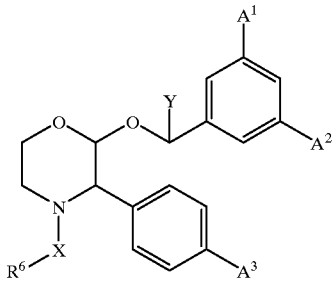

(IIa)

or a pharmaceutically acceptable salt thereof, wherein:
$A^1$ is fluorine or $CF_3$;
$A^2$ is fluorine or $CF_3$;
$A^3$ is fluorine or hydrogen;
$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;
$R^7$ is hydrogen, $C_{1-4}$alkyl, $C_{3-7}$cycloalkyl or $C_{3-7}$cycloalkyl$C_{1-4}$alkyl, or $C_{2-4}$alkyl substituted by $C_{1-4}$alkoxy or hydroxyl;
$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4,5 or 6 membered heteroaliphatic ring containing one or two heteroatoms selected from N, O and S;
or $R^7$, $R^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or S(O)$_2$ or a second nitrogen atom which will be part of a NH or NR$^c$ moiety where R$^c$ is $C_{1-4}$alkyl optionally substituted by hydroxy or $C_{1-4}$alkoxy;
or $R^7$, $R^8$ and the nitrogen atom to which they are attached form a non-aromatic azabicyclic ring system of 6 to 12 ring atoms;

or Z, $R^7$ and the nitrogen atom to which they are attached form a heteroaliphatic ring of 4 to 7 ring atoms which may optionally contain an oxygen ring atom;
X is an alkylene chain of 1 to 4 carbon atoms optionally substituted by oxo; and
Y is a $C_{1-4}$alkyl group optionally substituted by a hydroxyl group;
with the proviso that if Y is $C_{1-4}$alkyl, $R^6$ is susbstituted at least by a group of formula $ZNR^7R^8$ as defined above.

8. The method of claim 1 wherein the NK-1 receptor antagonist is a compound of formula (III):

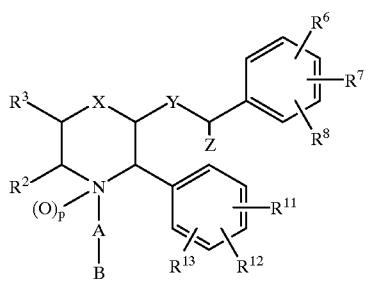

(III)

or a pharmaceutically acceptable salt thereof, wherein:

$R^2$ and $R^3$ are independently selected from the group consisting of:
(1) hydrogen,
(2) $C_{1-6}$alkyl,
(3) $C_{2-6}$alkenyl, and
(4) phenyl;
$R^6$, $R^7$ and $R^8$ are independently selected from the group consisting of:
(1) hydrogen,
(2) $C_{1-6}$alkyl,
(3) fluoro,
(4) chloro,
(5) bromo,
(6) iodo, and
(7) —$CF_3$;
$R^{11}$, $R^{12}$ and $R^{13}$ are independently selected from the group consisting of:
(1) fluoro,
(2) chloro,
(3) bromo, and
(4) iodo;
A is unsubstituted $C_{1-6}$alkyl;
B is selected from the group consisting of:

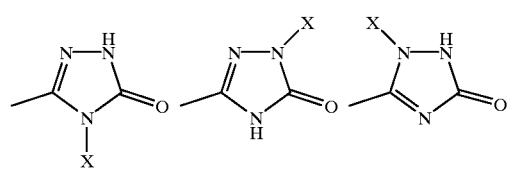

-continued

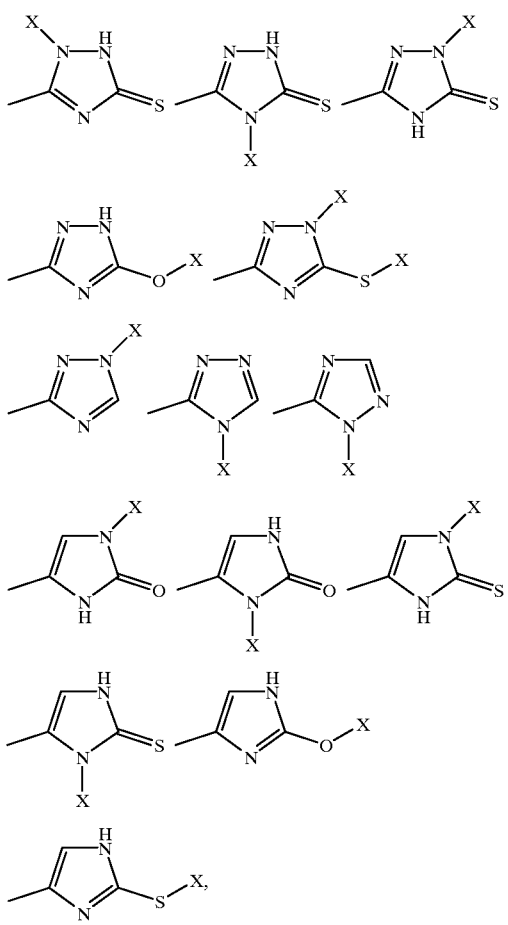

p is 0 or 1;

X is selected from:

(a) —PO(OH)O⁻•M⁺, wherein M⁺ is a pharmaceutically acceptable monovalent counterion, (b) —PO(O⁻)₂•2M⁺, (c) —PO(O⁻)₂•D²⁺, wherein D²⁺ is a pharmaceutically acceptable divalent counterion, (d) —CH(R⁴)—PO(OH)O⁻•M⁺, wherein R⁴ is hydrogen or $C_{1-3}$alkyl, (e) —CH(R⁴)—PO(O⁻)₂•2M⁺, (f) —CH(R⁴)—PO(O⁻)₂•D²⁺, (i) —CO—CH₂CH₂—CO₂⁻•M⁺, (j) —CH(CH₃)—O—CO—R⁵, wherein R⁵ is selected from the group consisting of:

(i) 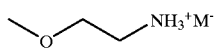

(ii) 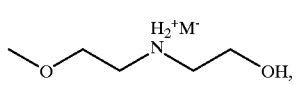

(iii) 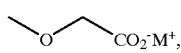

(iv) 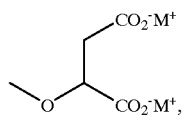

(v) 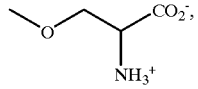

(vi) 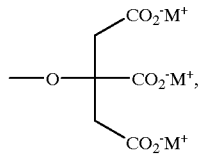

(vii) 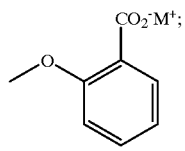

Y is —O—; and

Z is hydrogen or $C_{1-6}$alkyl.

9. The method of claim 1 wherein the NK-1 receptor antagonist is a compound of formula (IVa):

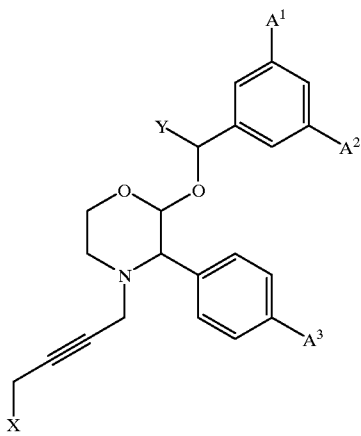

(IVa)

or a pharmaceutically acceptable salt thereof, wherein:

$A^1$ is fluorine or $CF_3$;

$A^2$ is fluorine or $CF_3$;

$A^3$ is fluorine or hydrogen;

X is a group of the formula $NR^6R^7$ or a C- or N-linked imidazolyl ring;

Y is hydrogen or $C_{1-4}$alkyl optionally substituted by a hydroxy group;

$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

$R^7$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by one or two substituents selected from $C_{1-4}$alkoxy, hydroxy or a 4, 5 or 6 membered heteroaliphatic ring containing one or two heteroatoms selected from N, O and S;

or $R^6$ and $R^7$, together with the nitrogen atom to which they are attached, form a saturated or partially saturated heterocyclic ring of 4 to 7 ring atoms, which ring may optionally contain in the ring one oxygen or sulphur atom or a group selected from $NR^8$, $S(O)$ or $S(O)_2$ and which ring may be optionally substituted by one or two groups selected from hydroxy$C_{1-4}$alkyl, $C_{1-4}$alkoxy$C_{1-4}$alkyl, oxo, $COR^a$ or $CO_2R^a$ where $R^a$ is hydrogen or $C_{1-4}$alkyl;

or $R^6$ and $R^7$ together with the nitrogen atom to which they are attached, form a non-aromatic azabicyclic ring system of 6 to 12 ring atoms; and $R^8$ is hydrogen, $C_{1-4}$alkyl, hydroxy$C_{1-4}$alkyl or $C_{1-4}$alkoxy$C_{1-4}$alkyl.

10. The method of claim 1 wherein the NK-1 receptor antagonist is a compound of formula (Va):

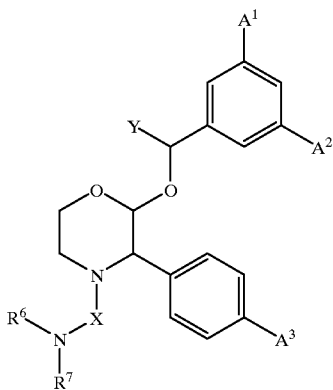

(Va)

or a pharmaceutically acceptable salt thereof, wherein:

$A^1$ is hydrogen, fluorine or $CF_3$;

$A^2$ is fluorine or $CF_3$;

$A^3$ is fluorine or hydrogen;

$R^6$ is hydrogen, $C_{1-6}$alkyl, $C_{3-7}$cycloalkyl, $C_{3-7}$cycloalkyl$C_{1-4}$alkyl, phenyl, or $C_{2-4}$alkyl substituted by $C_{1-4}$alkoxy or hydroxy;

$R^7$ is hydrogen, $C_{1-6}$alkyl, $C_{3-7}$cycloalkyl, $C_{3-7}$cycloalkyl$C_{1-4}$alkyl, phenyl, $C_{2-4}$alkyl substituted by $C_{1-4}$alkoxy or hydroxy, or the group $C(=NR^c)NR^aR^b$, where $R^a$ and $R^b$ are each independently hydrogen or $C_{1-4}$alkyl and $R^c$ is hydrogen, $C_{1-6}$alkyl, CN or $COR^a$;

or $R^6$ and $R^7$, together with the nitrogen atom to which they are attached, form a saturated heterocyclic ring of 4 to 7 ring atoms which may optionally contain in the ring one oxygen or sulphur atom or a group selected from $NR^8$, $S(O)$ or $S(O)_2$ and which ring may be optionally substituted by one or two groups selected from phenyl, benzyl, hydroxy$C_{1-4}$alkyl, $C_{1-4}$alkoxy$C_{1-4}$alkyl, hydroxy, oxo, $COR^a$ or $CO_2R^a$ where $R^a$ is as previously defined;

or $R^6$ and $R^7$, together with the nitrogen atom to which they are attached, form a piperidino ring substituted by a spiro-fused indene or indoline group, each of which may be unsubstituted or substituted on any available carbon atom by a group selected from $C_{1-6}$alkyl, $C_{1-6}$alkoxy, hydroxy, halogen, cyano, trifluoromethyl, $SO_2C_{1-6}$alkyl, $NR^aR^b$, $NR^aCOR^b$ or $CONR^aR^b$; or, in the case of an indoline group, on the nitrogen atom by a group selected from $C_{1-6}$alkyl, $C_{3-7}$cycloalkyl, $C_{3-7}$cycloalkyl$C_{1-4}$alkyl, phenyl$C_{1-4}$alkyl, $CO_2R^a$, $CONR^aR^b$, $SOR^a$ or $SO_2R^a$, where $R^a$ and $R^b$ are as previously defined;

$R^8$ is hydrogen, $C_{1-4}$alkyl, hydroxy$C_{1-4}$alkyl or $C_{1-4}$alkoxy$C_{1-4}$alkyl;

X is selected from —$CH_2CH_2$—, —$COCH_2$— or —$CH_2CO$—; and

Y is hydrogen, or $C_{1-4}$alkyl optionally substituted by a hydroxyl group.

11. The method of claim 1 wherein the antidepressant agent is selected from norepinephrine reuptake inhibitors, selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, atypical antidepressants, and noradrenergic and specific serotonergic antidepressants (NaSSAs).

12. The method of claim 1 wherein the anti-anxiety agent is selected from benzodiazepines, 5-$HT_{1A}$ agonists, antagonists or partial agonists, corticotropin releasing factor (CRF) antagonists and m1 muscarinic cholinergic receptor agonists.

13. An oral pharmaceutical composition comprising a NK-1 receptor antagonist and an antidepressant or anti-anxiety agent, together with at least one pharmaceutically acceptable carrier or excipient, characterised in that said NK-1 receptor antagonist is CNS-penetrant as determined by its ability to inhibit NK-1 receptor agonist-induced foot-tapping in the gerbil, and is effective in the attenuation of separation-induced vocalisations by guinea-pig pups.

14. A product comprising a NK-1 receptor antagonist and an antidepressant or anti-anxiety agent as a combined preparation for simultaneous, separate or sequential use in the treatment or prevention of depression or anxiety, characterised in that said NK-1 receptor antagonist is CNS-penetrant as determined by its ability to inhibit NK-1 receptor agonist-induced foot-tapping in the gerbil, and is effective in the attenuation of separation-induced vocalisations by guinea-pig pups.

* * * * *